US011154605B2

(12) United States Patent
Gibert Pérez et al.

(10) Patent No.: US 11,154,605 B2
(45) Date of Patent: Oct. 26, 2021

(54) **VACCINE COMPRISING *CLOSTRIDIUM* TOXOIDS**

(71) Applicant: HIPRA SCIENTIFIC, S.L.U., Girona (ES)

(72) Inventors: Xavier Gibert Pérez, Blanes (ES); Marta Sitjà Arnau, Girona (ES)

(73) Assignee: HIPRA SCIENTIFIC, S.L.U., Girona (ES)

( * ) Notice: Subject to any disclaimer, the term of this patent is extended or adjusted under 35 U.S.C. 154(b) by 0 days.

(21) Appl. No.: 16/620,846

(22) PCT Filed: Jun. 7, 2018

(86) PCT No.: PCT/EP2018/065025
§ 371 (c)(1),
(2) Date: Dec. 9, 2019

(87) PCT Pub. No.: WO2018/224595
PCT Pub. Date: Dec. 13, 2018

(65) Prior Publication Data
US 2020/0188500 A1 Jun. 18, 2020

(30) Foreign Application Priority Data
Jun. 9, 2017 (EP) ..................................... 17382358

(51) Int. Cl.
*A61K 39/08* (2006.01)
*A61K 9/00* (2006.01)
*A61K 39/00* (2006.01)

(52) U.S. Cl.
CPC ............ *A61K 39/08* (2013.01); *A61K 9/0019* (2013.01); *A61K 2039/552* (2013.01)

(58) Field of Classification Search
None
See application file for complete search history.

(56) References Cited

U.S. PATENT DOCUMENTS

| 2006/0233825 A1 | 10/2006 | Jayappa et al. |
| 2015/0140033 A1 | 5/2015 | Jayappa et al. |

FOREIGN PATENT DOCUMENTS

| WO | WO 2013/112867 A1 | 8/2013 |
| WO | WO 2014/144567 A2 | 9/2014 |

OTHER PUBLICATIONS

Dempster (Microbiol. Austr. 2015. 36: 120-121).*
International Search Report and Written Opinion dated Aug. 21, 2018 for PCT Application No. PCT/EP2018/065025, 13 pages.
Anderson, Michael A., et al: "Evaluation of two enzyme immunoassays for detection of Clostridium difficile toxins A and B in swine", *Vet erinary Microbiology*, vol. 128, pp. 2044-2206 (2008).
Ariza, W., et al., "Comparative study of two vaccines against neonatal diarrhea on a Canadian commercial farm", *48th Annual Meeting of the American Association of Swine Veterinarians* Feb. 25-28, 2017, pp. 198-202.
Arroyo, Luis G., et al: "PCR ribotyping of Clostridium difficile isolates originating from human and animal sources", *Journal of Medical Microbiology*, vol. 54, pp. 163-166 (2005).
Barroso, L. A., et al: "Nucleotide sequence of *Clostridium difficile* toxin B gene", *Nucleic Acids Research*, vol. 18, No. 13, p. 7499 (1990).
Carter, Glen P., et al: "The role of toxin A and toxin B in *Clostridium difficile*-associated disease. Past and present perspectives", *Nature*, vol. 1, Issue 1, pp. 58-64 (2010).
Chan, Gloria, et al: "The epidemiology of *Clostridium perfringens* type a on Ontario swine farms, with special reference to cpb2-positive isolates", *BMC Veterinary Research*, vol. 8, p. 156 (2012).
Cruz-Junior, Eduardo C., et al: "A surveillance of enteropathogens in piglets from birth to seven days of age in Brazil", *Pesqui. Vet. Bras.*, vol. 33, No. 8, pp. 963-969 (2013).
Debast, Sylvia. B., et al: "*Clostridium difficile* PCR ribotype 078 toxinotype V found in diarrhoeal pigs identical to isolates from affected humans", *Environmental Microbiology*, vol. 11, No. 2, pp. 505-511 (2009).
Dove, C. H., et al: "Molecular characterization of the *Clostridium difficile* toxin A gene", *Infection and Immunity*, vol. 58, pp. 480-488 (1990).
Hipra Laboratorios: Suiseng, for animal use only. URL:https://www.hipra.com/wcm/connect/hipra/17674953-a887-4690-9152-2c2e87883385/SUISENG-AFRICA-ZA-705520-00-2. (Jan. 1, 2017).
Justin, Neil, et al: "The first strain of *Clostridium perfringens* isolated from an avian source has an alpha-toxin with divergent structural and kinetic properties", *Biochemistry*, vol. 41, pp. 6253-6262 (2002).

(Continued)

*Primary Examiner* — Jennifer E Graser
(74) *Attorney, Agent, or Firm* — Squire Patton Boggs (US) LLP

(57) ABSTRACT

The present invention relates to an immunogenic composition comprising one or more *C. difficile* toxoid for use in a medicament for animals. The invention also encompasses an immunogenic composition comprising one or more *C. difficile* A toxoid and one or more *C. difficile* B toxoid and one or more *C. perfringens* Type A toxoid. The invention also encompasses vaccines comprising said immunogenic compositions, vaccines for use in the treatment and/or prevention of disease caused by *C. difficile* and *C. perfringens*, and kits thereof.

7 Claims, 10 Drawing Sheets
Specification includes a Sequence Listing.

(56) References Cited

OTHER PUBLICATIONS

Lawley, Trevor D., et al.: "Antibiotic treatment of *Clostridium difficile* carrier mice triggers a supershedder state, spore-mediated transmission, and severe disease in immunocompromised hosts", *Infection and Immunity*, vol. 77, No. 9, pp. 3661-3669 (2009).

Moreira, Gustavo, et al., "Immunogenicity of a Trivalent Recombinant Vaccine Against *Clostridium perfringens* Alpha, Beta, and Epsilon Toxins in Farm Ruminants", *Scientific Reports*, vol. 6, No. 1, p. 22816, XP055425656 (Mar. 23, 2016).

Songer, J. Glenn: "The emergence of *Clostridium difficile* as a pathogen of food animals", *Animal Health Research Revirews*, vol. 5, No. 2, pp. 321-326 (2004).

Songer, J. Glenn, et al: "Clostridial Enteric Infections in Pigs", *J. Vet. Diagnostic Investig.*, vol. 17, pp. 528-536 (2005).

Voth, Daniel E., et al: "*Clostridium difficile* Toxins: Mechanism of Action and Role in Disease", *Clinical Microbiology Reviews*, vol. 18, No. 2, pp. 247-263 (2005).

\* cited by examiner

A

B

A

B

C

D

E
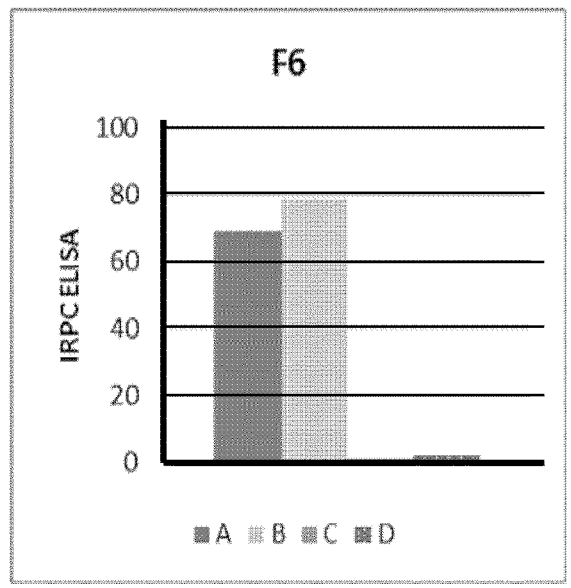
F
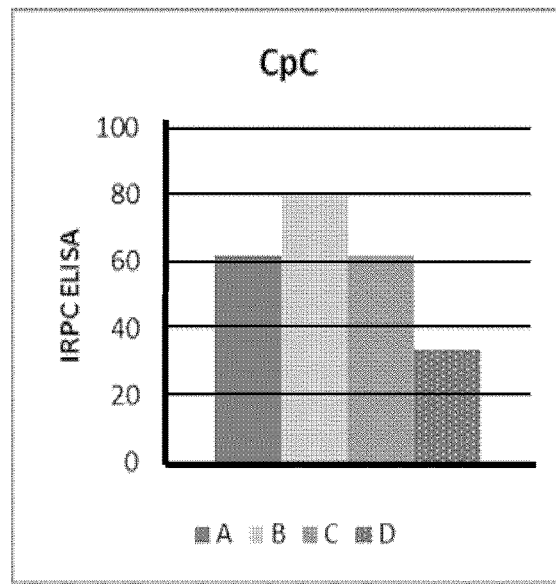
G
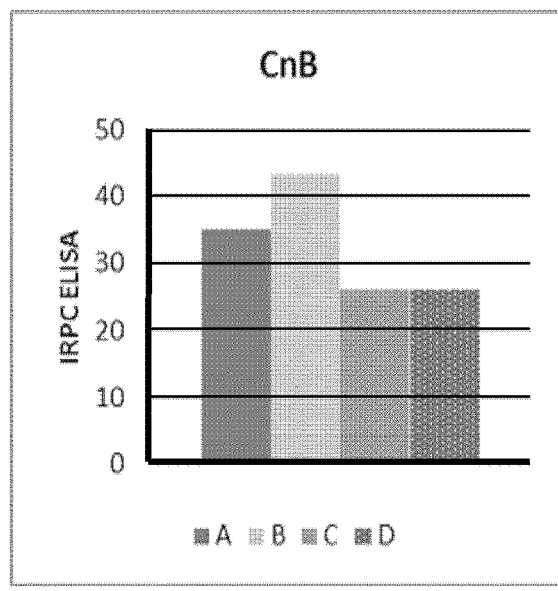
Cont. Fig. 2

A

B

C
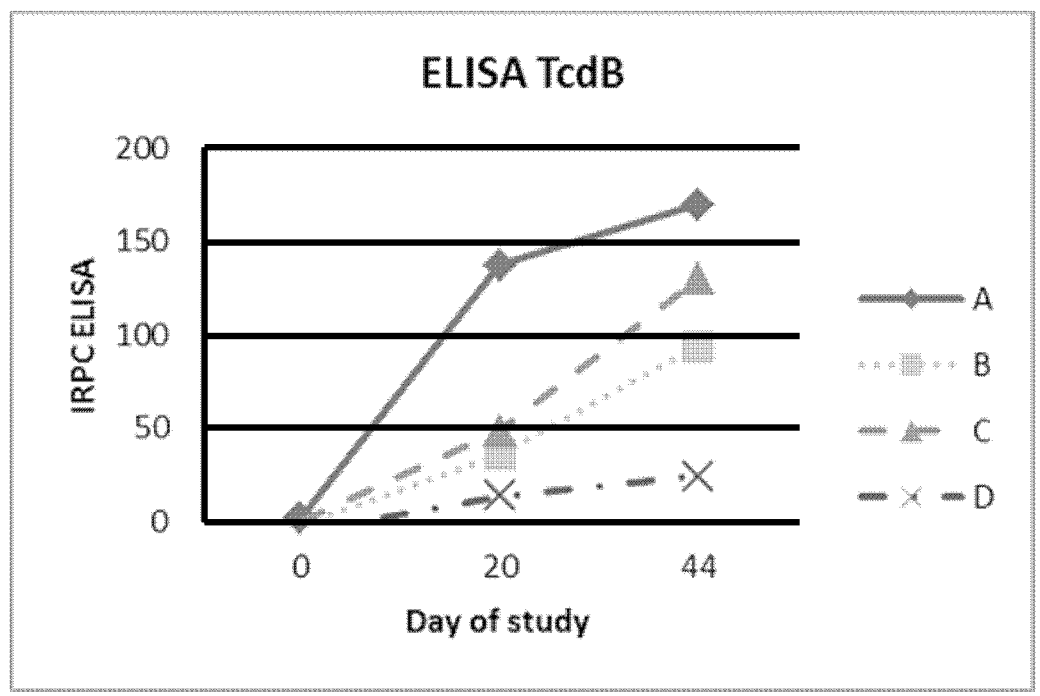
Cont. Fig. 3

A

B

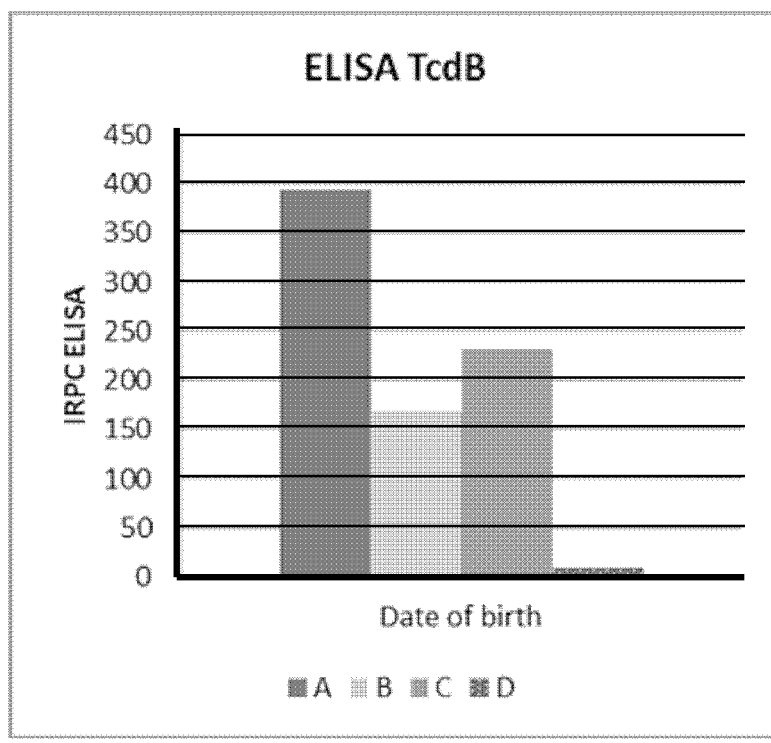
Cont. Fig. 4

A

B

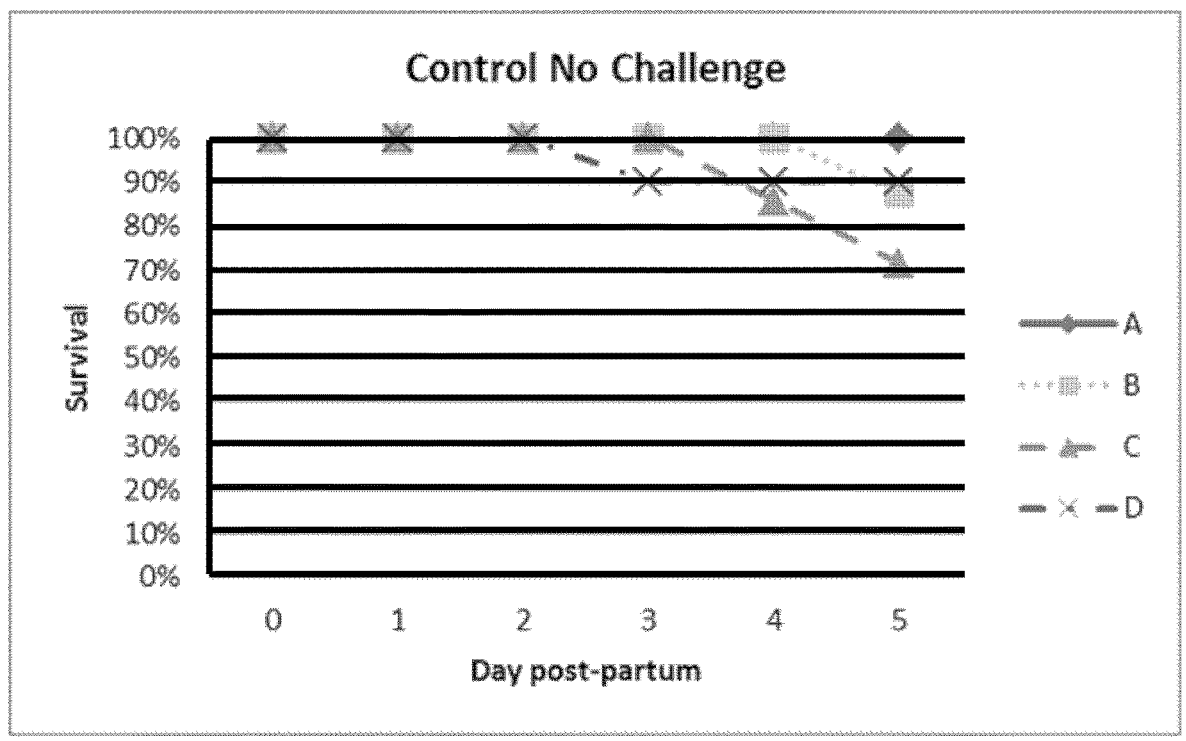
Cont. Fig. 5

VACCINE COMPRISING *CLOSTRIDIUM* TOXOIDS

CROSS REFERENCE TO RELATED APPLICATIONS

This is a National Stage application filed under 35 U.S.C. § 371 of International Application PCT/EP2018/065025 filed on Jun. 7, 2018, which designated the United States of America, the disclosure of which is incorporated herein by reference in the entirety and for all purposes. This application claims the benefit of priority to European Patent Application EP17382358.4, filed on Jun. 9, 2017.

This application claims the benefit of European Patent Application EP17382358.4 filed on Jun. 9, 2017.

TECHNICAL FIELD

The present invention relates to the field of immunological compositions and vaccines. More specifically, this invention relates to immunological compositions and vaccines comprising *Clostridium* toxoids, in particular *Clostridium difficile* toxoids and mixtures of *C. difficile* toxoids with *C. perfringens* Type A toxoids; and the use of said immunological compositions and vaccines to protect animals against clostridial diseases.

BACKGROUND ART

Clostridia are Gram-positive spore-forming anaerobic bacteria. Clostridia produce the largest number of toxins of any type of bacteria. They are widely recognized as pathogens of both domestic and wild animals. Of the currently known clostridial species, *Clostridium difficile* (*C. difficile*) and *Clostridium perfringens* (*C. perfringens*) are often considered to be the most widely occurring bacterial pathogens, and are particularly relevant as causal agents of enteric disease in domestic animals. Their pathogenicity lies in the production of a number of exotoxins.

*C. difficile* infection has been described in humans, pigs, horses, non-human primates, rabbits, rats, dogs, hamsters and cats (Arroyo L. G. et al., 2005; Debast S. B. et al., 2009). The vast majority of cases are associated with disruption of the intestinal microbiota as may be commonly observed with antibiotic treatment or in neonatal animals with undeveloped microbiota (Lawley T. D. et al., 2009).

Exotoxins A (TcdA, an enterotoxin) and B (TcdB, a cytotoxin) are considered the major virulence factors associated with disease (Carter G. P. et al., 2010; Voth D. E. et al., 2005). The TcdA and TcdB toxins are part of the large clostridia glycosylating toxin family with molecular masses of 308 and 269 kDA, respectively. The genetic sequences encoding both toxigenic proteins A and B have been elucidated (Barroso et al., 1990; Dove et al., 1990). *C. difficile* also produces other toxins, such as the Binary toxin (CDT), which is associated with increased severity of *C. difficile* infection.

*C. difficile* is also an important enteric pathogen in pigs during the first week of life. *Clostridium difficile*-associated disease (CDAD) develops in piglets 1 to 7 days of age, born to gilts or multiparous sows. The history includes early-onset scours, rarely with respiratory distress, and sudden death. There is usually edema of the mesocolon and the colon may have pasty-to-watery yellowish contents. Songer and others have shown that in *C. difficile* affected porcine herds, up to two-thirds of the litters can be diseased, and within the litter, the morbidity can be as high as 97-100% (Anderson M. A. et al., 2008; Songer J. G. et al., 2004). Common gross and histologic lesions associated with *C. difficile* infections in piglets include mesocolonic edema and purulent ulcerative colitis, respectively.

Although the awareness of this disease has increased in swine production over the last decade, more research is needed to better understand epidemiology, prevention and treatment. Experimental vaccines against *C. difficile* have been tested in different animals. For instance, patent application WO2014144567A2 discloses a method of inactivating *C. difficile* toxins A and B and the use of compositions comprising the resulting toxoids for immunization in hamsters. Currently, there are no commercial vaccines available to protect livestock, such as swine, against *C. difficile*.

Among *Clostridium* species, on the other hand, *C. perfringens* is the major toxin producer and is also the most widespread, being found as part of the microbiota of animals and humans and also in soil. *C. perfringens* is a gram-positive, anaerobic, fermentative, spore-forming *bacillus* that is classified into different biotypes, designated A through E according to the production of major toxins: alpha toxin, beta toxin, epsilon toxin and iota toxin. Other toxins such as beta-2 toxin, theta toxin, mu toxin, delta toxin, kappa toxin, lambda toxin, *Clostridium* enterotoxin CPE, necrotic enteritis B-like toxin (NetB) are also produced by *C. perfringens* strains. In veterinary medicine, *C. perfringens* is responsible for several, mostly enteric, diseases. *C. perfringens* Type A infections are common causes of enteric diseases in pigs, diarrhea in neonatal piglets and other animals. *C. perfringens* Type A is considered by some researchers as the main cause of neonatal diarrhea in piglets (Songer J. G. et al., 2005; Chan et al., 2012). In the past decade, diagnosis of neonatal piglet diarrhea due to *C. perfringens* Type A has increased, and has been associated with increased pre-weaning mortality. *C. perfringens* Type A commonly affects neonates in the first week of life. The disease is described as a non-hemorrhagic mucoid diarrhea and is characterized by mucosal necrosis and villus atrophy, without attachment and invasion by the microorganism (Songer J. G. et al., 2005). According to some studies, lesions may also be absent; in light of this, some groups have stated that *C. perfringens* diarrhea in neonatal piglets might be secretory (Songer J. G. et al., 2005; Cruz-Junior E. C. et al., 2013). Diagnostic of *Clostridium perfringens* Type A is very difficult due the impossibility to differentiate between pathogenic and commensal *C. perfringens* Type A (Songer J. G. et al., 2005). Beta-2 toxin was postulated as a specific swine pathogenic factor for *Clostridium perfringens* Type A affecting pigs but this fact is still under discussion.

*C. perfringens* alpha toxin is a large known toxin and their sequence and structure has been elucidated. The mature protein is 370 amino acids long and has a molecular weight of 43 kDa (Justin N. et al., 2002).

Current efforts to control *C. perfringens* rely upon sanitary measures and use of antibiotics in animal feed. Vaccines for the protection of pigs against *C. perfringens* Type A are rare. There is currently only one vaccine commercially available (Clostriporc A, IDT Biologika GmbH, Germany). One of the reasons for this may be the fact that *C. perfringens* Type A is a member of the normal flora. Vaccination against *C. perfringens* Type A has been described, for example, using toxoids or recombinant toxins—as detailed in the patent application US20150140033A1 for other animal species such as poultry. However, it seems that *C. perfringens* Type A does not induce sufficient immune stimulation to be efficient for preventing and controlling diarrhea in swine.

In the field of pig farm production, it is important to note that clostridial diseases often occur concurrently; therefore it is highly desirable to simultaneously protect the animals from several bacterial species. However the administration of several vaccines often involves multiple injections and there are several problems associated to this approach—for instance, the complexity of the administration procedure and larger injection volumes. For both the animal and the practitioner, it is desirable to inject all necessary antigens in one vaccine of normal volume, thus rendering the vaccination procedure less traumatic and painful for the animal, and more efficient and easier to manage for the practitioner.

Furthermore, protection of newborns from infections is critical given their greater vulnerability. Indeed, pre-weaning mortality of piglets accounts for an important loss to the pig industry. Although piglets are often treated with antibiotics, there are several problems associated to this method of treatment: antibiotics are costly; there is a high degree of disease recurrence following withdrawal of treatment; and there are increasing concerns related to the promotion of bacterial resistance. Therefore, new approaches to reduce antibiotic treatments in food-producing animals are desirable.

Active immunization of clostridia to piglets through vaccines is not a current practice—the immaturity of their immune system renders them unable to mount an effective immune response. This fact is particularly difficult when the vaccine is aimed to be administered to one-day-old piglets or from their first day of life. However, it is known that piglet vaccination may take advantage of the postnatal maternal supply of passive immunity that occurs through the colostrum of the sow. Therefore, piglets can be indirectly immunized against a given pathogen by actively immunizing the sow from which they are lactating. This process is quite complex and several factors are of importance: the lactational secretions of the sow must contain adequate amounts of the appropriate immunoglobulin (i.e. IgG before gut closure and IgA post-closure); the immunoglobulins must be delivered intact to the site of absorption or functional activity, and finally in the case of IgG, the immunoglobulins must be absorbed intact and delivered to the circulation of the piglet. Consequently, there is a need to develop new vaccines that are effective for passive immunization of piglets through the colostrum of the sow from their first day of life.

At present, there are no specific vaccines in the market against *C. difficile*. More importantly, nor are there combination vaccines against *C. difficile* and *C. perfringens* Type A for swine in a single vaccine. As a result, there is a need for new and effective vaccines against *C. difficile* and *C. perfringens* to protect domestic animals, such as swine. In particular, there is a need to reduce the mortality rate of piglets and to reduce the risk of zoonotic transmission of Clostridia to humans.

SUMMARY OF INVENTION

Inventors have found that the administration of toxoids from different species of *Clostridium* elicits an effective immune response in livestock, such as in swine, which protects them from clostridial diseases. Unexpectedly, protection by these vaccines comprising the toxoids of *Clostridium* is in addition efficiently transferred to the progeny of the animals, which acquire maternal passive immunity through lactation already on their first day after birth.

Thus, in a first aspect, the invention provides an immunogenic composition comprising one or more *Clostridium difficile* (*C. difficile*) toxoids for use as a medicament in livestock.

In a second aspect, the present invention provides also a vaccine for use as a medicament in livestock, comprising: (a) an immunogenic composition comprising one or more *C. difficile* toxoids, and (b) a pharmaceutically acceptable excipient and/or carrier.

Surprisingly, the inventors discovered that immunogenic compositions, comprising *C. difficile* toxoids, were able to protect swine from infections from said bacteria. This is of particular importance, not only for the pig industry but also for the health of human populations, because animal feces are a major zoonotic reservoir of the disease. To the best of inventor's knowledge, this is the first vaccine with the capacity to effectively immunize livestock against *C. difficile*. In addition, the composition of the invention is also suitable to be transferred to the progeny of the treated animals, which acquire effective passive immunity from their first day of life.

A third aspect of the invention relates to an immunogenic composition, comprising (a) one or more *C. difficile* toxoids selected from the group consisting of a *C. difficile* A toxoid (TcdA), a *C. difficile* B toxoid (TcdB), and mixtures thereof; and (b) one or more *C. pefringens* Type A toxoids.

A fourth aspect of the invention relates to a vaccine comprising the said immunogenic composition as defined in the third aspect of the invention and a pharmaceutically acceptable excipient and/or carrier.

These third and fourth aspects result from the finding that a combination of toxoids of *C. difficile* and toxoids of *C. perfringens* can elicit an efficient immune response in livestock, in particular in swine, even circumventing antigenic interference. Indeed, active antibodies against *C. difficile* and *C. perfringens* toxins are present in the serum of the vaccinated specimens and, in the particular case of pregnant livestock females, these maternal antibodies pass to the progeny in an active form through lactation. Therefore, vaccines of the invention suppose a real hit in the field of livestock raising, in particular swine raising: for minimizing dead indexes in progeny, even at first day of life and thus increasing livestock production, in particular, swine production; because it supposes an efficient immunization in all specimens (vaccinated females and immunization of progeny through lactation); and for reducing the risk of zoonotic infections.

Accordingly, a fifth aspect of the invention relates to the immunogenic composition as defined in the third aspect of the invention, or the vaccine as defined in the fourth aspect of the invention for use as a medicament, which is for use in a method of providing maternal passive immunity to the progeny of a livestock female, particularly by means of lactation, the method comprising administering the immunogenic composition or the vaccine to the pregnant female livestock animal prior to the birth of the progeny.

A sixth aspect of the invention relates to a process for making the vaccine of the invention, which comprises the step of mixing the immunogenic composition described above with a pharmaceutically acceptable excipient and/or carrier.

A seventh aspect of the invention relates to a vaccination kit comprising:
(a) an immunogenic composition as defined above;
(b) a pharmaceutically acceptable excipient and/or carrier;
(c) optionally, an adjuvant; and
(d) optionally, instructions for its use.

The ELISA IRPC (relative index×100) is represented on the y-axis as an indicator of the IgG antibody response against *E. coli* F4ab fimbrial adhesin (A), F5 fimbrial adhesin (B), F4ac fimbrial adhesin (C), LT enterotoxin (D) and F6 fimbrial adhesin (E); *C. perfringens* Type C toxoid (F); and *C. novyi* B toxoid (G).

Figure 2:
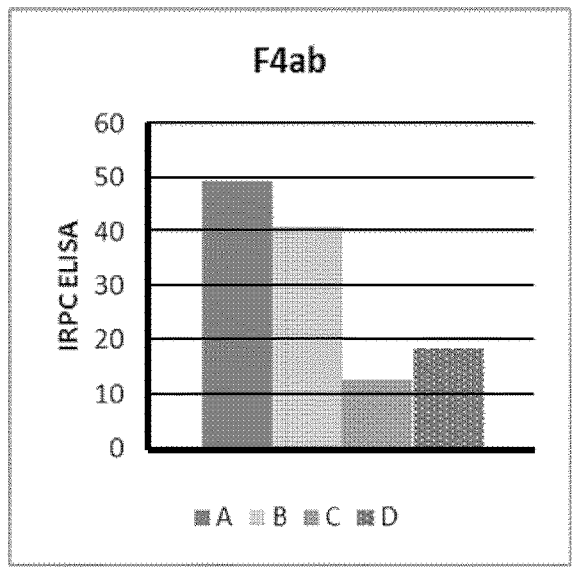
FIG. 2, related with Example 3, is a bar diagram showing the serologic response of sows immunized with different combination vaccines at day 44 after first injection, groups A to D. Groups A and B correspond to sows vaccinated with *C. difficile*, *C. perfringens* Type A, *C. perfringens* Type C, *C. novyi* Type B and *E. coli*; group C corresponds to sows vaccinated with *C. difficile* and *C. perfringens* Type A; and group D corresponds to sows vaccinated with a placebo vaccine.
Figure 2:
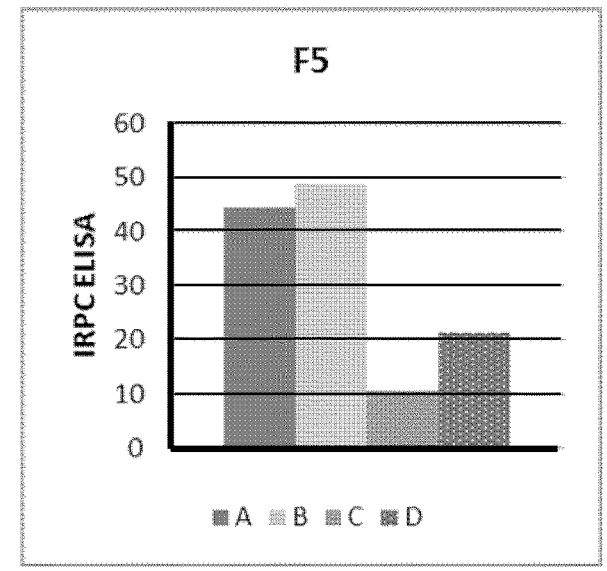
Figure 2:
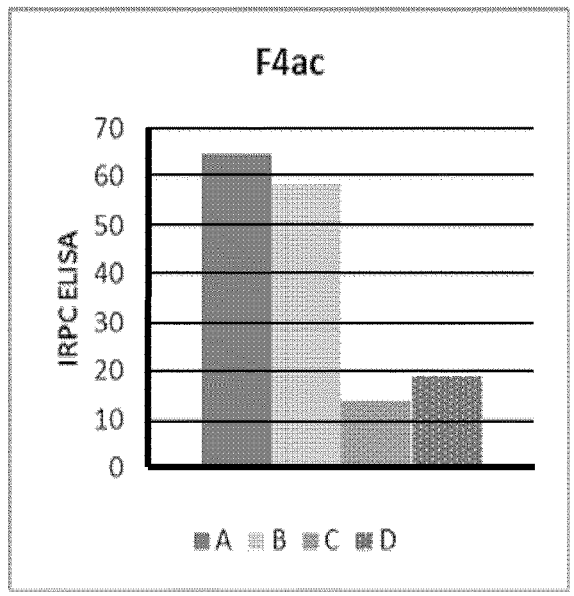
Figure 2:
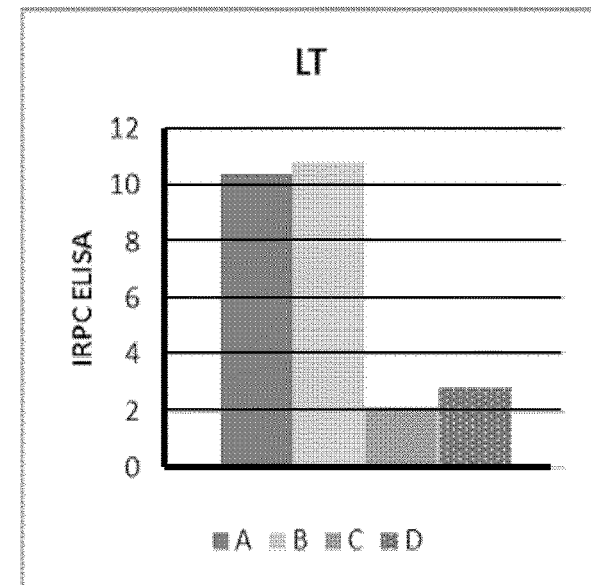
Figure 3:
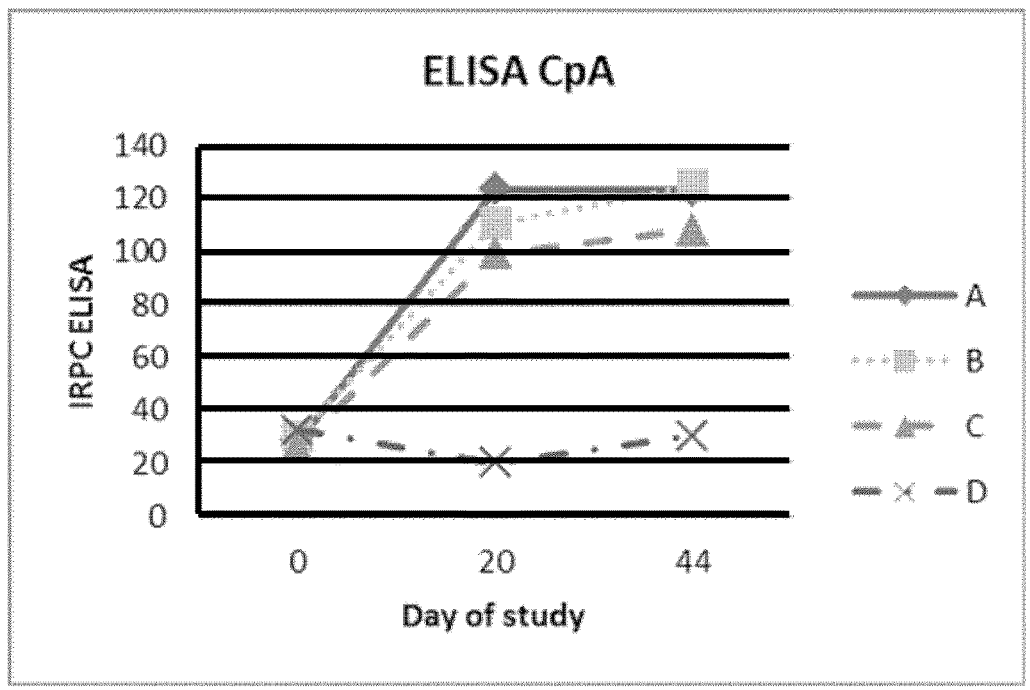
Figure 3:
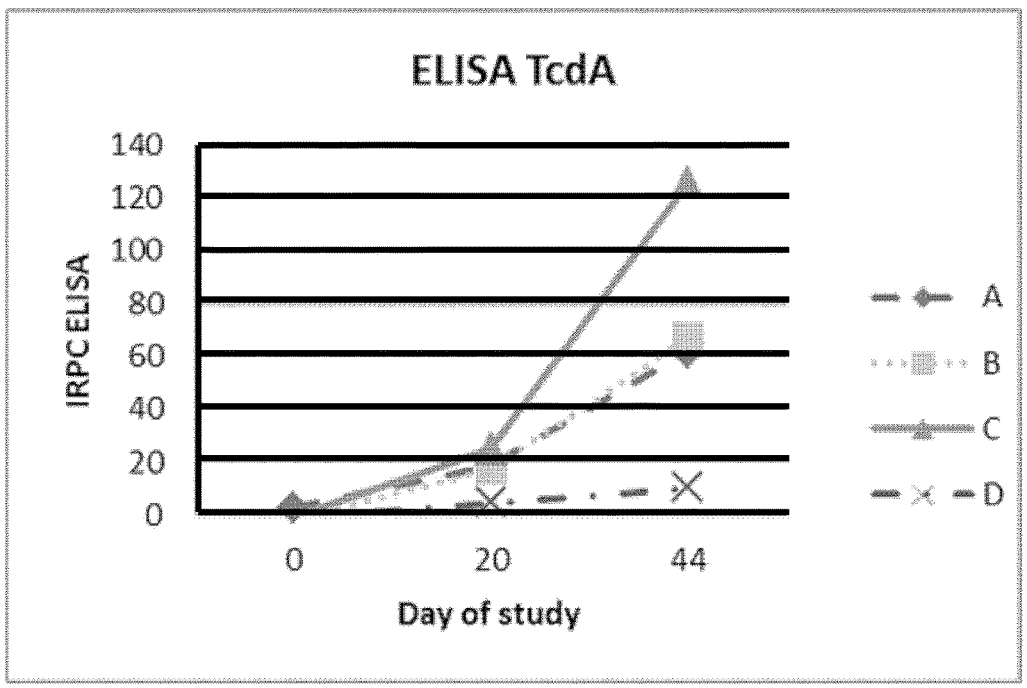

FIG. 3, related with Example 3, shows the serologic response to the *C. perfringens* Type A CpA (A) and *C. difficile* TcdA (B) and TcdB (C) toxoids. Groups A to D as defined in FIG. 2. The ELISA IRPC (relative index x 100) is represented on the y-axis as an indicator of the IgG antibody response.

Figure 4:
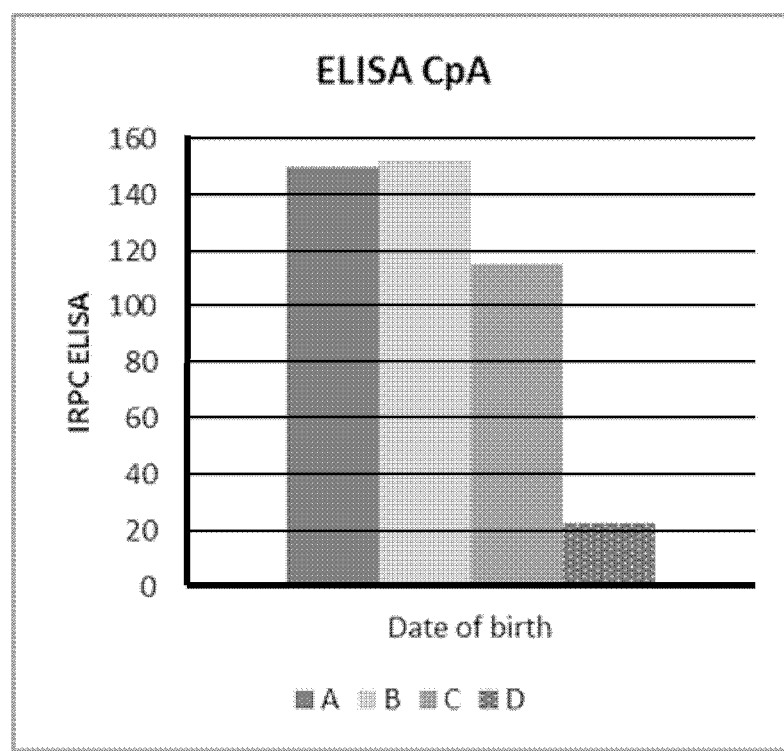
Figure 4:
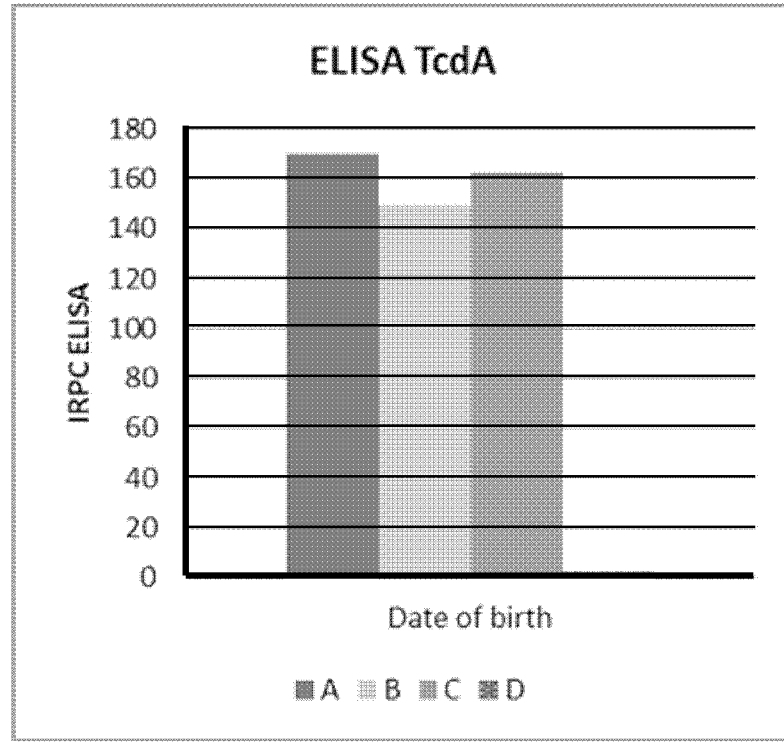

FIG. 4, related with Example 3, shows the antibody titers against the antigens of *C. perfringens* Type A CpA (A), and *C. difficile* TcdA (B) and TcdB (C) toxoids in the colostrum of vaccinated sows. Groups A to D as defined in FIG. 2 (Group A in first left-column, group B in second column, group C in third column and D in fourth column). The ELISA IRPC (relative index x 100) is represented on the y-axis FIG. 5, related with Example 4, shows the survival curves of piglets that had been passively immunized with different combination vaccines and then challenged with either *C. perfringens* Type A (A), *C. difficile* (B), or not challenged (C), groups A to D as defined in FIG. 2. The day post-partum of the piglets is represented on the x-axis, and the survival rate is on the y-axis.

Figure 6:
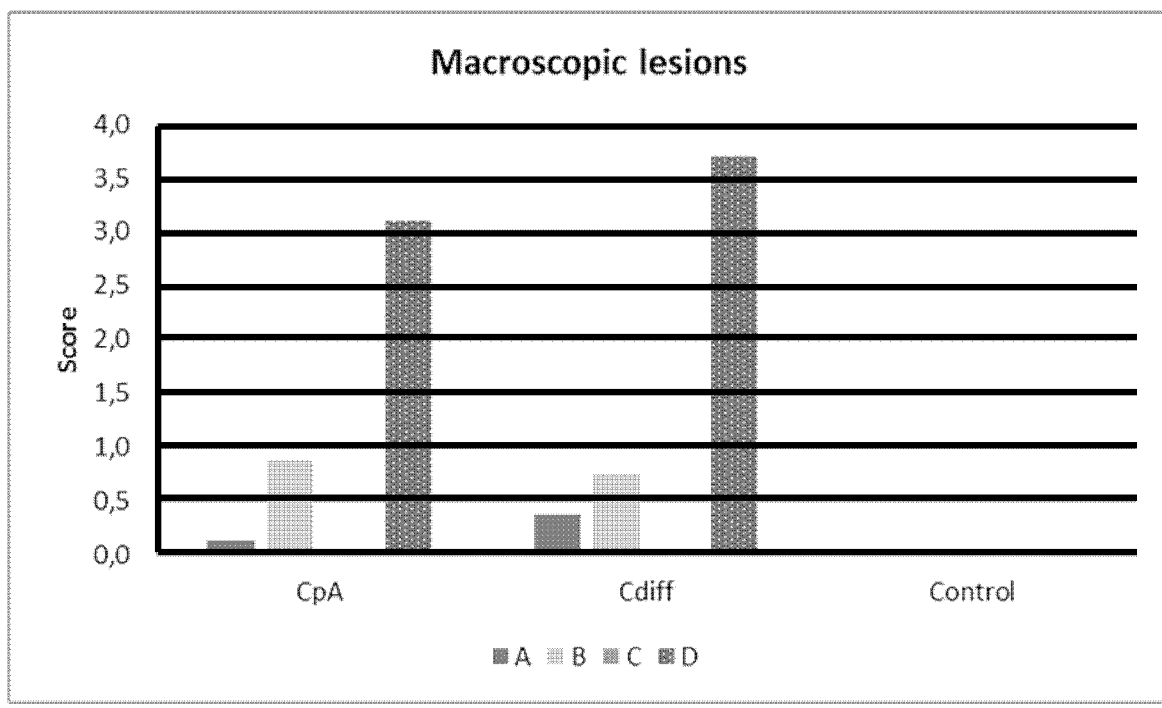

FIG. 6, related with Example 4, is a bar diagram showing the result of a macroscopic lesion analysis of piglets that had been passively immunized with different combination vaccines, then challenged with either *C. difficile* or *C. perfringens* Type A, and finally humanely euthanized for analysis 5 days after the challenge. Groups A to D as defined in FIG. 2 (Group A in first left-column, group B in second column, group C in third column and D in fourth column). The x-axis represents the type of challenge and the y-axis shows the score used to quantify the macroscopic lesions (as defined in Example 4).

DETAILED DESCRIPTION OF THE INVENTION

Unless defined otherwise, all technical and scientific terms used herein have the same meaning as is commonly understood by one of skill in the art to which this invention belongs at the time of filling. However, in the event of any latent ambiguity, definitions provided herein take precedent over any dictionary or extrinsic definition. Further, unless otherwise required by context, singular terms shall include pluralities and plural terms shall include the singular.

As used herein, the term "immunogenic" or "immunological composition" refers to material, which elicits an immunological response in the host of a cellular or antibody-mediated immune response type to the composition upon administration to a vertebrate, including humans. The immunogenic composition comprises molecules with antigenic properties, such as immunogenic polypeptides. An immunogenic polypeptide is generally referred to as antigenic. A molecule is "antigenic" when it is capable of specifically interacting with an antigen recognition molecule of the immune system, such as an immunoglobulin (antibody) or T cell antigen receptor. An antigenic polypeptide contains an epitope of at least about 5, and particularly at least about 10, at least 15, at least 20 or at least 50 amino acids. An antigenic portion of a polypeptide, also referred to as an epitope, can be that portion that is immunodominant for antibody or T cell receptor recognition, or it can be a portion used to generate an antibody to the molecule by conjugating the antigenic portion to a carrier polypeptide for immunization. The immunogenic composition relates according to this description, to the active molecule, composition comprising said molecule, or composition comprising more than one antigenic molecule to which a particular immune reaction is desired. Examples of immunogenic compositions include the supernatants of microorganism cultures, including bacteria, protozoa and viruses. Said supernatants contain those antigenic molecules of interest for initiating an immune response against thereto and that have been released (exotoxins) or delivered to the culture media where microorganisms grew and after the microorganism cells or particles (viruses) have been separated. The supernatants are also termed herewith as cell-free preparations.

The term "antigen" refers to a molecule against which a subject can initiate an immune response, e.g. a humoral and/or cellular immune response. Depending on the intended function of the composition, one or more antigens may be included.

As for the expression "immunologically effective amount", or "immunologically effective dose" means the administration of that amount or dose of antigen, either in a single dose or as part of a series, that elicits, or is able to elicit, an immune response that reduces the incidence of or lessens the severity of infection or incident of disease in an animal for either the treatment or prevention of disease. The immunologically effective amount or effective dose is also able for inducing the production of antibody for either the treatment or prevention of disease. This amount will vary depending upon a variety of factors, including the physical condition of the subject, and can be readily determined by someone of skill in the art.

The term "medicament" as used herein is synonymous of a pharmaceutical or veterinary drug (also referred to as medicine, medication, or simply drug) use to cure, treat or prevent disease in animals, including humans, as widely accepted. Drugs are classified in various ways. One key distinction is between traditional small-molecule drugs, usually derived from chemical synthesis, and biopharmaceuticals, which include recombinant proteins, vaccines, blood products used therapeutically (such as IVIG), gene therapy, monoclonal antibodies and cell therapy (for instance, stem-cell therapies). In the present invention, medicament preferably is a veterinary medicament, and even more preferably is a vaccine for veterinary use.

The term "vaccine" as used herein, means an immunogenic composition of the invention accompanied by adequate excipients and/or carriers, that when administered to an animal, elicits, or is able to elicit, directly or indirectly, an immune response in the animal. Particularly, the vaccines of the present invention elicit an immunological response in the host of a cellular or antibody-mediated type upon administration to the subject that it is protective. The vaccine may be a "combination vaccine". The term "combination vaccine" means that the vaccine contains various antigens in a single preparation, protecting against two or more diseases or against one disease caused by two or more microorganisms. Thus, the vaccine includes as "active ingredient" an "immunogenic composition" according to the invention.

The term "toxoid" as used herein means bacterial toxin whose toxicity has been inactivated or suppressed either by chemical, molecular or heat treatment, while other properties, typically immunogenicity, are maintained. Thus, when used during vaccination, an immune response is mounted and immunological memory is formed against the molecular markers of the toxoid without resulting in toxin-induced illness. Particular examples of procedures for obtaining a toxoid derived from a bacterial toxin include the treatment of a bacterial culture with a composition comprising formaldehyde. Furthermore, the inactivated toxoids may be separated from the cells (for example by centrifugation means). The supernatant is then filtered (i.e. by tangential ultrafiltration) through filters of a desired molecular weight cut-off, in order to enrich or to concentrate resulting solution in the desired toxoid. By this methodology, concentrated supernatants containing the purified inactivated toxins (toxoids) are obtained. However, toxoids present in the bacterial growth media (in particular, in the invention in clostridia media) without separation or further purification steps are also encompassed in the scope of the invention and in the "toxoid" definition as used herein.

Most of the toxoids have the same polypeptide sequence as the toxin from which they derive from. Thus, when particular sequences are indicated in the present invention, it is recited indistinctly the term toxin or toxoid.

The term "livestock" relates to domesticated or farm animals raised to produce commodities such us food. Particularly, it relates to food-producing animals such as cattle, sheep, goats, swine, poultry (including egg-producing poultry), and equine animal. More in particular, it relates to food-producing animals such as cattle, sheep, goats, swine, and equine animals. Even more in particular, in the present invention relates to swine species.

The term "carrier" is to be understood as a pharmaceutically acceptable component other than the immunogenic component. The carrier can be organic, inorganic, or both. Suitable carriers well known to those of skill in the art and include, without limitation, large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

As used herein, the term "host" or "subject" is intended for the target individuals in need thereof to whom the immunogenic composition or vaccine of the invention are administered, among others humans, mammals, livestock, or any other animal species susceptible to be vaccinated with the compositions of the invention. Preferably, the mammal is a porcine specie, more preferably is a swine, and more preferably is a pregnant sow, gilt or piglet.

As used herein, the term "pig" or "swine" is intended for porcine species including, among others, pigs, boars, sows, gilts and piglets of any age or in any phase of their production cycle; it is particularly intended for sows and gilts, and more particularly for piglets. A gilt is a female pig approximately under the age of 1 year. The term refers to a pig who has not farrowed, or given birth to a litter or progeny. Once a pig has had a litter or progeny and is past approximately her first year, the pig is known as sow.

As used herein, the terms "maternal passive immunization" and "maternal passive immunity", which are used indistinctly, refer to the transfer of the immunological response of an immunogenic composition or a vaccine from the mother to the progeny, generally by the transmission of maternal antibodies specific against an infectious agent, so that as result thereof, an immune protective response, or passive protection, that reduces the incidence of or lessens the severity of infection or incident of a disease is elicited in the progeny. Maternal passive immunity can be accomplished inter alia through the ingestion of colostrum and/or milk by lactation, as occurs in mammals, or the absorption of antibodies in the bloodstream through the placenta, for example, or alternatively, via the egg in avian species. Maternal passive immunization is achieved by administering an immunogenic composition or a vaccine to a pregnant female livestock, particularly a gilt or a sow before parturition, i.e., before the birth of the litter or progeny. Alternatively, in avian species, transfer of maternal antibodies (MAb) to their offspring is done through the egg yolk where the antibodies are absorbed and enter into the circulatory system.

As above exposed, the inventors propose for the first time an immunogenic composition comprising at least a *C. difficile* toxoid, or which is the same, one or more *C. difficile* toxoids, and a vaccine comprising said immunogenic composition for use as a medicament in livestock, in particular, for use in swine.

All particular embodiments of the immunogenic composition for use as a medicament disclosed herewith apply also to the vaccine for use as a medicament comprising said immunogenic composition.

In a particular embodiment, the immunogenic composition or the vaccine comprising it is for use as a medicament in swine. More in particular is for use in swine selected from the group consisting of pigs, boars, sows, gilts and piglets.

In another particular embodiment, optionally in combination with any embodiment above or below, the immunogenic composition and the vaccine comprising it, is for use in the prevention and/or treatment of a disease caused by *Clostridium* sp. in livestock. This embodiment can also be formulated as the use of the immunogenic composition or of the vaccine as defined above for the manufacture of a medicament, for the treatment and/or prevention of enteric infections or disease caused by *Clostridium* sp. in livestock. This embodiment can also be formulated as a method of immunizing livestock in need thereof with an immunologically effective amount of an immunogenic composition or a vaccine as defined above, in particular for treating and/or preventing enteric infections or disease caused by Clostridium sp. Particularly, when livestock is swine. More particularly, the immunogenic composition or the vaccine is for use in preventing and/or treating enteric infections or disease caused by *C. difficile*.

Particularly, the immunogenic composition and the vaccine are for use in preventing and/or treating enteric infections or disease caused by *Clostridium* sp., in particular *C. difficile*.

In another particular embodiment, the *C. difficile* toxoid of the immunogenic composition of the first aspect is selected from the group consisting of a *C. difficile* A toxoid, a *C. difficile* B toxoid, a *C. difficile* binary toxoid (CDT) and mixtures thereof. More particularly, the toxoids of the immunogenic composition are selected from the group consisting of a *C. difficile* A toxoid, a *C. difficile* B toxoid, and mixtures thereof. More particularly, the toxoids of the immunogenic composition are a *C. difficile* A toxoid and a *C. difficile* B toxoid. That is, the immunogenic composition comprises one *C. difficile* A toxoid and one *C. difficile* B toxoid.

In a particular embodiment of the first aspect, optionally in combination with any embodiment above or below, the immunogenic composition for use as described above comprises an A toxin derived from a *C. difficile* strain, an A toxoid derived from said toxin, and/or an immunogenic fragment of said toxin or said toxoid, wherein the toxoid and fragment of said toxoid is immunologically effective, which means that is able to elicit an immune response.

In another particular embodiment of the first aspect, optionally in combination with any embodiment above or below, the immunogenic composition for use as described above comprises a B toxin derived from a *C. difficile* strain, a B toxoid derived from said toxin, and/or an immunogenic fragment of said toxin or said toxoid, wherein the toxoid and fragment of said toxoid is immunologically effective, which means that is able to elicit an immune response.

In a particular embodiment of the first aspect, optionally in combination with any embodiment above or below, the immunogenic composition for use as described above comprises a *C. difficile* A toxoid which is derived from a *C. difficile* A toxin which comprises SEQ ID NO: 1, or a sequence that has at least a 80% sequence identity with SEQ ID NO: 1. More particularly, the *C. difficile* A toxin comprises SEQ ID NO: 1. Even more particularly, the *C. difficile* A toxin consists of SEQ ID NO: 1.

In another particular embodiment, the *C. difficile* A toxoid is derived from a *C. difficile* A toxin that has a sequence identity of 80%, 81%, 82%, 83%, 84%, 85%, 86%, 87%, 88%, 89%, 90%, 91%, 92%, 93%, 94%, 95%, 96%, 97%, 98% or 99% with SEQ ID NO: 1.

In another particular embodiment of the first aspect, optionally in combination with any embodiment above or below, the immunogenic composition for use as described above comprises a *C. difficile* B toxoid which is derived from a *C. difficile* B toxin which comprises SEQ ID NO: 2, or a sequence that has at least a 80% sequence identity with SEQ ID NO: 2. More particularly, the *C. difficile* B toxin comprises SEQ ID NO: 2. Even more particularly, the *C. difficile* B toxin consists of SEQ ID NO: 2.

In another particular embodiment, the *C. difficile* B toxoid is derived from a *C. difficile* B toxin that has a sequence identity of 80%, 81%, 82%, 83%, 84%, 85%, 86%, 87%, 88%, 89%, 90%, 91%, 92%, 93%, 94%, 95%, 96%, 97%, 98% or 99% with SEQ ID NO: 2.

In yet a more particular embodiment of the immunogenic composition, it comprises at least the *C. difficile* A toxoid that consists of SEQ ID NO: 1 toxin sequence, and at least the *C. difficile* B toxoid that consists of SEQ ID NO: 2 toxin sequence. More particularly, the toxoids A, and B are present in a ratio from 99:0.1 to 0.1:99, particularly from 50:0.5 to 0.5:50, more in particular from 10:1 to 1:10. In particular from 5:1 to 1:5, more in particular, from 2.5:1 to 1:2.5. Yet more in particular the toxoids A, and B are present in a ratio 2.5:1.

In a particular embodiment of the first aspect, optionally in combination with any embodiment above or below, the immunogenic composition further comprises at least a *C. perfringens* toxoid. Or which is the same, one or more *C. perfringens* toxoids. Particularly, the toxoid is selected from the group consisting of alpha toxoid, beta toxoid, beta-2 toxoid, epsilon toxoid, theta toxoid, mu toxoid, delta toxoid, iota toxoid, kappa toxoid, lambda toxoid, CPE enterotoxoid, NetB toxoid and mixtures thereof. In particular a *C. perfringens* Type A toxoid, particularly alpha toxoid, beta-2 toxoid, theta toxoid, mu toxoid, CPE enterotoxoid, NetB toxoid and mixtures thereof. More particularly, the toxoid is a *C. perfringens* Type A alpha toxoid.

In another particular embodiment of the first aspect, optionally in combination with any embodiment above or below, the immunogenic composition for use as described above further comprises an alpha toxin derived from a *C. perfringens* strain, an alpha toxoid derived from said toxin, and/or an immunogenic fragment of said toxin or said toxoid, wherein the toxoid and fragment of said toxoid is immunologically effective, which means that is able to elicit an immune response.

Combining various antigens in a single immunogenic composition or in a vaccine comprising said immunogenic composition is commonly sought in the field of immunization. This is of particular importance when the pathogens against which protection is pursued are usually found together in infections. However, development of combined immunogenic compositions or combined vaccines is not straightforward. It has been found that simple mixing of the components of a combination immunogenic compositions or vaccine is complicated by the fact that not all antigens can be effectively combined together. The reduction in the immunogenicity of an antigen when combined with other components—as compared to the particular antigen administered alone—is known as interference. A further problem encountered in the formulation of combination vaccines is the inherent stability of their composite antigens over time. Vaccines in solution may undergo processes over time which decrease the immunogenicity of its antigen components, for instance the degradation of the antigen or the desorption of the antigens from the adjuvant to which they had been adsorbed.

Considering the state of the art, it was unexpected that combining together in a single immunogenic composition toxoids of different *Clostridium* species would provide an effective and safe immunization of subjects. This is particularly true for the immunization against *C. difficile*, which has been sought for a long time in different animal species. More importantly, it was highly unforeseen that the immunization achieved by the combination immunogenic compositions (i.e. combination vaccine with the immunogenic compositions) could be passively transferred to the newborns and an effective protection in neonatal piglets could be obtained as well, even from their first day of life.

Thus, in a second aspect, the present invention provides a vaccine for use as a medicament in livestock, comprising: (a) an immunogenic composition comprising one or more *C. difficile* toxoids, and (b) a pharmaceutically acceptable excipient and/or carrier.

In a particular embodiment of the first and second aspects, optionally in combination with any embodiment above or below, the immunogenic compositions or the vaccine for use as described above are for use in preventing and/or treating enteric infections or diseases caused by *C. difficile*, *C. perfringens*, and mixtures thereof.

In another particular embodiment of the first and second aspects, optionally in combination with any embodiment above or below, the immunogenic compositions or the vaccine for use as described above comprises a *C. perfringens* Type A alpha toxoid which is derived from a *C. perfringens* Type A alpha toxin which comprises SEQ ID NO: 3, or a sequence that has at least a 80% sequence identity with SEQ ID NO: 3. More particularly, the *C. perfringens* Type A alpha toxin comprises SEQ ID NO: 3. Even more particularly, the *C. perfringens* Type A alpha toxin consists of SEQ ID NO: 3.

In another particular embodiment, the *C. perfringens* Type A alpha toxoid is derived from a *C. perfringens* Type A alpha toxin that has a sequence identity of 80%, 81%, 82%, 83%, 84%, 85%, 86%, 87%, 88%, 89%, 90%, 91%, 92%, 93%, 94%, 95%, 96%, 97%, 98% or 99% with SEQ ID NO: 3.

In another particular embodiment of the first and second aspects, the immunogenic compositions or the vaccine comprising it, comprises one *C. difficile* A toxoid, one *C. difficile* B toxoid, and one *C. perfringens* Type A toxoid, particularly one *C. perfringens* Type A alpha toxoid.

In yet a more particular embodiment of the first and second aspects, the immunogenic compositions or the vaccine comprising it, comprises the *C. difficile* A toxoid that consists of SEQ ID NO: 1 toxin sequence, the *C. difficile* B toxoid that consists of SEQ ID NO: 2 toxin sequence, and the *C. perfringens* Type A alpha toxoid that consists of SEQ ID NO: 3 toxin sequence.

The amino acid sequences of the toxins of all the aspects of the invention are given in Table 1.

TABLE 1

| Toxin | SEQ ID No. | Amino acid sequence |
|---|---|---|
| *C. difficile* A toxin (Gen Bank accession number P16154; version P16154.2) | 1 | MSLISKEELIKLAYSIRPRENEYKTILTNLDEYNKLTTNNNENKYL QLKKLNESIDVFMNKYKTSSRNRALSNLKKDILKEVILIKNSNTSP VEKNLHFVWIGGEVSDIALEYIKQWADINAEYNIKLWYDSEAFLV NTLKKAIVESSTTEALQLLEEEIQNPQFDNMKFYKKRMEFIYDR QKRFINYYKSQINKPTVPTIDDIIKSHLVSEYNRDETVLESYRTNS LRKINSNHGIDIRANSLFTEQELLNIYSQELLNRGNLAAASDIVRL LALKNFGGVYLDVDMLPGIHSDLFKTISRPSSIGLDRWEMIKLEA IMKYKKYINNYTSENFDKLDQQLKDNFKLIIESKSEKSEIFSKLEN LNVSDLEIKIAFALGSVINQALISKQGSYLTNLVIEQVKNRYQFLN QHLNPAIESDNNFTDTTKIFHDSLFNSATAENSMFLTKIAPYLQV GFMPEARSTISLSGPGAYASAYYDFINLQENTIEKTLKASDLIEF KFPENNLSQLTEQEINSLWSFDQASAKYQFEKYVRDYTGGSLS EDNGVDFNKNTALDKNYLLNNKIPSNNVEEAGSKNYVHYIIQLQ GDDISYEATCNLFSKNPKNSIIQRNMNESAKSYFLSDDGESILE LNKYRIPERLKNKEKVKVTFIGHGKDEFNTSEFARLSVDSLSNEI SSFLDTIKLDISPKNVEVNLLGCNMFSYDFNVEETYPGKLLLSIM DKITSTLPDVNKNSITIGANQYEVRINSEGRKELLAHSGKWINKE EAIMSDLSSKEYIFFDSIDNKLKAKSKNIPGLASISEDIKTLLLDAS VSPDTKFILNNLKLNIESSIGDYIYYEKLEPVKNIIHNSIDDLIDEFN LLENVSDELYELKKLNNLDEKYLISFEDISKNNSTYSVRFINKSN GESVYVETEKEIFSKYSEHITKEISTIKNSIITDVNGNLLDNIQLDH TSQVNTLNAAFFIQSLIDYSSNKDVLNDLSTSVKVQLYAQLFSTG LNTIYDSIQLVNLISNAVNDTINVLPTITEGIPIVSTILDGINLGAAIK ELLDEHDPLLKKELEAKVGVLAINMSLSIAATVASIVGIGAEVTIFL LPIAGISAGIPSLVNNELILHDKATSVVNYFNHLSESKKYGPLKTE DDKILVPIDDLVISEIDFNNNSIKLGTCNILAMEGGSGHTVTGNID HFFSSPSISSHIPSLSIYSAIGIETENLDFSKKIMMLPNAPSRVFW WETGAVPGLRSLENDGTRLLDSIRDLYPGKFYWRFYAFFDYAIT TLKPVYEDTNIKIKLDKDTRNFIMPTITTNEIRNKLSYSFDGAGGT YSLLLSSYPISTNINLSKDDLWIFNIDNEVREISIENGTIKKGKLIKD VLSKIDINKNKLIIGNQTIDFSGDIDNKDRYIFLTCELDDKISLIIEIN LVAKSYSLLLSGDKNYLISNLSNTIEKINTLGLDSKNIAYNYTDES NNKYFGAISKTSQKSIIHYKKDSKNILEFYNDSTLEFNSKDFIAED INVFMKDDINTITGKYYVDNNTDKSIDFSISLVSKNQVKVNGLYL NESVYSSYLDFVKNSDGHHNTSNFMNLFLDNISFWKLFGFENIN FVIDKYFTLVGKTNLGYVEFICDNNKNIDIYFGEWKTSSSKSTIFS GNGRNVVVEPIYNPDTGEDISTSLDFSYEPLYGIDRYINKVLIAP DLYTSLININTNYYSNEYYPEIIVLNPNTFHKKVNINLDSSSFEYK WSTEGSDFILVRYLEESNKKILQKIRIKGILSNTQSFNKMSIDFKD IKKLSLGYIMSNFKSFNSENELDRDHLGFKIIDNKTYYYDEDSKL VKGLININNSLFYFDPIEFNLVTGWQTINGKKYYFDINTGAALTSY KIINGKHFYFNNDGVMQLGVFKGPDGFEYFAPANTQNNNIEGQ AIVYQSKFLTLNGKKYYFDNNSKAVTGWRIINNEKYYFNPNNAIA AVGLQVIDNNKYYFNPDTAIISKGWQTVNGSRYYFDTDTAIAFN GYKTIDGKHFYFDSDCVVKIGVFSTSNGFEYFAPANTYNNNIEG QAIVYQSKFLTLNGKKYYFDNNSKAVTGLQTIDSKKYYFNTNTA EAATGWQTIDGKKYYFNTNTAEAATGWQTIDGKKYYFNTNTAI ASTGYTIINGKHFYFNTDGIMQIGVFKGPNGFEYFAPANTDANNI EGQAILYQNEFLTLNGKKYYFGSDSKAVTGWRIINNKKYYFNPN NAIAAIHLCTINNDKYYFSYDGILQNGYITIERNNFYFDANNESKM VTGVFKGPNGFEYFAPANTHNNNIEGQAIVYQNKFLTLNGKKY YFDNDSKAVTGWQTIDGKKYYFNLNTAEAATGWQTIDGKKYYF NLNTAEAATGWQTIDGKKYYFNTNTFIASTGYTSINGKHFYFNT |

TABLE 1-continued

| Toxin | SEQ ID No. | Amino acid sequence |
|---|---|---|
| | | DGIMQIGVFKGPNGFEYFAPANTDANNIEGQAILYQNKFLTLNG
KKYYFGSDSKAVTGLRTIDGKKYYFNTNTAVAVTGWQTINGKK
YYFNTNTSIASTGYTIISGKHFYFNTDGIMQIGVFKGPDGFEYFA
PANTDANNIEGQAIRYQNRFLYLHDNIYYFGNNSKAATGWVTID
GNRYYFEPNTAMGANGYKTIDNKNFYFRNGLPQIGVFKGSNGF
EYFAPANTDANNIEGQAIRYQNRFLHLLGKIYYFGNNSKAVTGW
QTINGKVYYFMPDTAMAAAGGLFEIDGVIYFFGVDGVKAPGIYG |
| C. difficile B toxin (Gen Bank accesion number P18177; version P18177.3) | 2 | MSLVNRKQLEKMANVRFRTQEDEYVAILDALEEYHNMSENTVV
EKYLKLKDINSLTDIYIDTYKKSGRNKALKKFKEYLVTEVLELKNN
NLTPVEKNLHFVWIGGQINDTAINYINQWKDVNSDYNVNVFYDS
NAFLINTLKKTVVESAINDTLESFRENLNDPRFDYNKFFRKRMEII
YDKQKNFINYYKAQREENPELIIDDIVKTYLSNEYSKEIDELNTYI
EESLNKITQNSGNDVRNFEEFKNGESFNLYEQELVERWNLAAA
SDILRISALKEIGGSMYLDVDMLPGIQPDLFESIEKPSSVTVDFWE
MTKLEAIMKYKEYIPEYTSEHFDMLDEEVQSSFESVLASKSDKS
EIFSSLGDMEASPLEVKIAFNSKGIINQGLISVKDSYCSNLIVKQIE
NRYKILNNSLNPAISEDNDFNTTTNTFIDSIMAEANADNGRFMM
ELGKYLRVGFFPDVKTTINLSGPEAYAAAYQDLLMFKEGSMNIH
LIEADLRNFEISKTNISQSTEQEMASLWSFDDARAKAQFEEYKR
NYFEGSLGEDDNLDFSQNIVVDKEYLLEKISSLARSSERGYIHYI
VQLQGDKISYEAACNLFAKTPYDSVLFQKNIEDSEIAYYYNPGD
GEIQEIDKYKIPSIISDRPKIKLTFIGHGKDEFNTDIFAGFDVDSLS
TEIEAAIDLAKEDISPKSIEINLLGCNMFSYSINVEETYPGKLLLKV
KDKISELMPSISQDSIIVSANQYEVRINSEGRRELLDHSGEWINK
EESIIKDISSKEYISFNPKENKITVKSKNLPELSTLLQEIRNNSNSS
DIELEEKVMLTECEINVISNIDTQIVEERIEEAKNLTSDSINYIKDE
FKLIESISDALCDLKQQNELEDSHFISFEDISETDEGFSIRFINKET
GESIFVETEKTIFSEYANHITEEISKIKGTIFDTVNGKLVKKVNLDT
THEVNTLNAAFFIQSLIEYNSSKESLSNLSVAMKVQVYAQLFST
GLNTITDAAKVVELVSTALDETIDLLPTLSEGLPIIATI IDGVSLGA
AIKELSETSDPLLRQEIEAKIGIMAVNLTTATTAIITSSLGIASGFSI
LLVPLAGISAGIPSLVNNELVLRDKATKVVDYFKHVSLVETEGVF
TLLDDKIMMPQDDLVISEIDFNNNSIVLGKCEIWRMEGGSGHTV
TDDDIDHFFSAPSITYREPHLSIYDVLEVQKEELDLSKDLMVLPNA
PNRVFAWETGWTPGLRSLENDGTKLLDRIRDNYEGEFYWRYF
AFIADALITTLKPRYEDTNIRINLDSNTRSFIVPIITTEYIREKLSYS
FYGSGGGTYALSLSQYNMGINIELSESDVWIIDVDNVVRDVTIESD
KIKKGDLIEGILSTLSIEENKIILNSHEINFSGEVNGSNGFVSLTFSI
LEGINAIIEVDLLSKSYKLLISGELKILMLNSNHIQQKIDYIGFNSEL
QKNIPYSFVDSEGKENGFINGSTKEGLFVSELPDVVLISKVYMD
DSKPSFGYYSNNLKDVKVITKDNVNILTGYYLKDDIKISLSLTLQD
EKTIKLNSVHLDESGVAEILKFMNRKGNTNTSDSLMSFLESMNI
KSIFVNFLQSNIKFILDANFIISGTTSIGQFEFICDENDNIQPYFIKF
NTLETNYTLYVGNRQNMIVEPNYDLDDSGDISSTVINFSQKYLY
GIDSCVNKVVISPNIYTDEINITPVYETNNTYPEVIVLDANYINEKI
NVNINDLSIRYVWSNDGNDFILMSTSEENKVSQVKIRFVNVFKD
KTLANKLSFNFSDKQDVPVSEIILSFTPSYYEDGLIGYDLGLVSL
YNEKFYINNFGMMVSGLIYINDSLYYFKPPVNNLITGFVTVGDDK
YYFNPINGGAASIGETIIDDKNYYFNQSGVLQTGVFSTEDGFKY
FAPANTLDENLEGEAIDFTGKLIIDENIYYFDDNYRGAVEWKELD
GEMHYFSPETGKAFKGLNQIGDYKYYFNSDGVMQKGFVSIND
NKHYFDDSGVMKVGYTEIDGKHFYFAENGEMQIGVFNTEDGFK
YFAHHNEDLGNEEGEEISYSGILNFNNKIYYFDDSFTAVVGWKD
LEDGSKYYFDEDTAEAYIGLSLINDGQYYFNDDGIMQVGFVTIN
DKVFYFSDSGIIESGVQNIDDNYFYIDDNGIVQIGVFDTSDGYKY
FAPANTVNDNIYGQAVEYSGLVRVGEDVYYFGETYTIETGWIYD
MENESDKYYFNPETKKACKGINLIDDIKYYFDEKGIMRTGLISFE
NNNYYFNENGEMQFGYINIEDKMFYFGEDGVMQIGVFNTPDGF
KYFAHQNTLDENFEGESINYTGWLDLDEKRYYFTDEYIAATGSV
IIDGEEYYFDPDTAQLVISE |
| C. perfringens Type A alpha toxin (Gen Bank accesion number WP_011590041; version WP_011590041.1) | 3 | MKRKICKALICAALATSLWAGASTKVYAWDGKIDGTGTHAMIVT
QGVSILENDLSKNEPESVRKNLEILKENMHELQLGSTYPDYDKN
AYDLYQDHFWDPDTDNNFSKDNSWYLAYSIPDTGESQIRKFSA
LARYEWQRGNYKQATFYLGEAMHYFGDIDTPYHPANVTAVDS
AGHVKFETFAEERKEQYKINTAGCKTNEAFYTDILKNKDFNAWS
KEYARGFAKTGKSIYYSHASMSHSWDDWDYAAKVTLANSQKG
TAGYIYRFLHDVSEGNDPSVGKNVKELVAYISTSGEKDAGTDD
YMYFGIKTKDGKTQEWEMDNPGNDFMTGSKDTYTFKLKDENL
KIDDIQNMWIRKRKYTAFSDAYKPENIKIIANGKVVVDKDINEWIS
GNSTYNIK |

When in the present invention identity with a sequence (in particular between amino acid sequences) is mentioned, this is preferably determined by using the BLASTP algorithm disclosed in Altschul, S. F., et. al. "Gapped BLAST and PSI-BLAST: a new generation of protein database search programms", *Nucleic Acids Research* —1997, Vol. No. 25, pp. 3389-3402, and NCBI http://www.ncbi.nlm.nih.gov/BLAST. A particular percentage of identity encompasses variations of the sequence due to conservative mutations of one or more amino acids leading to a protein being still effective, thus able to elicit an immune response without being toxic. Protein variations are also due to insertions or deletions of one or more amino acids.

The alpha toxoid of the immunogenic composition of any of the aspects of the invention, can be derived from the alpha toxin naturally encoded by a *C. perfringens* cell, the A toxoid can be derived from the A toxin naturally encoded by a *C. difficile* cell, and the B toxoid can be derived from the B toxin naturally encoded by a *C. difficile* cell. In particular, any strain of *C. difficile* producing A (TcdA) and B (TcdB) toxins and any strain of *C. perfringens*, particularly *C. perfringens* Type A, producing alpha toxins can be used in the method of the invention, i.e., the strain can be selected, among others, from field strains, collection strains or genetically modified strains. The different toxoids can be obtained from the same strain or from different strains. The skilled man in the art perfectly knowns how to identify whether a *Clostridium* sp. strain produces a specific toxin by using routinely microbiological techniques.

Alternatively, the toxoids of the immunogenic compositions or vaccines of the invention are derived from toxins which are recombinant polypeptides, i.e., are encoded by a gene that had been genetically manipulated.

In addition, the toxoids can be contained in a whole cell preparation or in a cell-free preparation. As whole cell preparation is to be understood that the toxoid is comprised in a composition also comprising the cell components, usually in these cell components in form of a cell lysate. On the other hand, a cell-free preparation is to be understood as a composition comprising the toxoid, this later being optionally purified (isolated) from a medium in which the cells previously grew. Preferably, it is a cell-free preparation comprising the toxoid.

The toxoids can be obtained by chemical treatment, protease cleavage, recombinant DNA methods by making fragments or mutations of the toxins (e.g. point mutations) or by thermal treatment of the corresponding toxins by routinary means known by the skilled in the art. In particular, treatment with BEI (binary ethylenimine), acetylethylenimine, beta-propiolactone, detergents (such as TWEEN®, TRITON® X or alkyl trimethylammonium salts) and glutaraldehyde are examples of suitable chemical inactivating agents for use in inactivate bacterial toxins of the invention. Other chemical inactivating agent is formalin or formaldehyde. The inactivation can be performed using standard methods known to those of skill in the art. In one embodiment, formaldehyde is preferably used in toxoid preparation. One embodiment uses about 0.1 to 1% of a solution of formaldehyde to inactivate clostridia toxins.

In a particular embodiment for any of the aspects of the invention, the toxoids of *C. difficile* are obtainable by a method comprising the steps of:
(a) growing under anaerobic conditions, at least one strain of *C. difficile* producing the toxin or toxins of interest, in particular producing a *C. difficile* A toxin and/or a *C. difficile* B toxin;
(b) inactivating the *C. difficile* culture;
(c) optionally separating the *C. difficile* cells from the supernatant; and
(d) optionally concentrating the supernatant of step (c) to obtain a concentrated supernatant.

In a particular embodiment for any of the aspects of the invention, the toxoids of *C. difficile* are obtainable by a method comprising the steps of:
(a) growing under anaerobic conditions, at least one strain of *C. difficile* producing the toxin or toxins of interest, in particular producing a *C. difficile* A toxin and/or a *C. difficile* B toxin; and
(b) inactivating the *C. difficile* culture.

In a particular embodiment for any of the aspects of the invention, the toxoids of *C. difficile* are obtainable by a method comprising the steps of:
(a) growing under anaerobic conditions, at least one strain of *C. difficile* producing the toxin or toxins of interest, in particular producing a *C. difficile* A toxin and/or a *C. difficile* B toxin;
(b) inactivating the *C. difficile* culture;
(c) separating the *C. difficile* cells from the supernatant; and
(d) concentrating the supernatant of step (c) to obtain a concentrated supernatant.

In a particular embodiment for any of the aspects of the invention, the toxoids of *C. difficile* are obtainable by a method comprising the steps of:
(a) growing under anaerobic conditions, at least one strain of *C. difficile* producing the toxin or toxins of interest, in particular producing a *C. difficile* A toxin and/or a *C. difficile* B toxin;
(b) separating the *C. difficile* cells from the supernatant;
(c) concentrating the supernatant of step (b) to obtain a concentrated supernatant; and
(d) inactivating the *C. difficile* toxins in the supernatant.

In the same way, in another particular embodiment for any of the aspects of the invention, the toxoids of *C. perfringens* are obtainable by a method comprising the steps of:
(a) growing under anaerobic conditions, at least one strain of *C. perfringens* producing the toxin or toxins of interest, in particular producing a *C. perfringens* Type A toxin, more particularly, *C. perfringens* type A alpha toxin;
(b) inactivating the *C. perfringens* culture;
(c) optionally separating the *C. perfringens* cells from the supernatant; and
(d) optionally concentrating the supernatant of step (c) to obtain a concentrated supernatant.

In another particular embodiment for any of the aspects of the invention, the toxoids of *C. perfringens* are obtainable by a method comprising the steps of:
(a) growing under anaerobic conditions, at least one strain of *C. perfringens* producing the toxin or toxins of interest, in particular producing a *C. perfringens* Type A toxin, more particularly, *C. perfringens* type A alpha toxin; and
(b) inactivating the *C. perfringens* culture.

In another particular embodiment for any of the aspects of the invention, the toxoids of *C. perfringens* are obtainable by a method comprising the steps of:
(a) growing under anaerobic conditions, at least one strain of *C. perfringens* producing the toxin or toxins of interest, in particular producing a *C. perfringens* Type A toxin, more particularly, *C. perfringens* type A alpha toxin;
(b) inactivating the *C. perfringens* culture;
(c) separating the *C. perfringens* cells from the supernatant; and
(d) concentrating the supernatant of step (c) to obtain a concentrated supernatant.

In another particular embodiment for any of the aspects of the invention, the toxoids of *C. perfringens* are obtainable by a method comprising the steps of:
(a) growing under anaerobic conditions, at least one strain of *C. perfringens* producing the toxin or toxins of interest, in particular producing a *C. perfringens* Type A toxin, more particularly, *C. perfringens* type A alpha toxin;
(b) separating the *C. perfringens* cells from the supernatant;
(c) concentrating the supernatant of step (b) to obtain a concentrated supernatant; and
(d) inactivating the *C. perfringens* toxins in the supernatant.

In another particular embodiment, optionally in combination with any embodiment above or below, the immunogenic composition for use according to the first aspect and the vaccine for use according to the second aspect have an immunologically effective amount of *C. difficile* A toxoid from 0.1 to 100% (v/v), particularly from 0.5 to 50% (v/v), and more particularly from 1 to 25% (v/v), even more in particular from 1 to 10%.

In another particular embodiment, optionally in combination with any embodiment above or below, the immunogenic composition for use according to the first aspect and the vaccine for use according to the second aspect have an immunologically effective amount of *C. difficile* B toxoid from 0.1 to 100% (v/v), particularly from 0.5 to 50% (v/v), and more particularly from 1 to 25% (v/v), even more in particular from 1 to 10%.

In another particular embodiment, optionally in combination with any embodiment above or below, the immunogenic composition for use according to the first aspect and the vaccine for use according to the second aspect have an immunologically effective titer of *C. difficile* toxoids A and B (TcdA/TcdB) of at least 5.0 cytopathic titre (CPE, $\log_{10}$CPE/ml), titrated based on the cytopathic effect before the inactivation step. Particularly of at least 5.5, of at least 6.0, of at least 6.5, of at least 7.0, of at least 7.5, of at least 8.0, of at least 8.5, of at least 9.0, of at least 9.5, of at least, 10.0, of at least 10.5, or of at least 11.0 CPE. Preferably, between 5.0 and 11.0 CPE, more preferably, between 6.5 and 9.5 CPE. The CPE assay is a routine method for the toxic effect titration. The details of the procedure are described below and are well-known by any person skilled in the art.

In yet another particular embodiment, optionally in combination with any embodiment above or below, the immunogenic composition for use according to the first aspect and the vaccine for use according to the second aspect, the *C. difficile* toxoids A and B (TcdA/TcdB) are present in a ratio 99:0.1 to 0.1:99, particularly from 50:0.5 to 0.5:50, more particularly from 10:1 to 1:10, particularly 5:1 to 1:5, more particularly 2.5:1 to 1:2.5 and more particularly 2.5:1.

In yet another particular embodiment, optionally in combination with any embodiment above or below, the immunogenic composition for use according to the first aspect and the vaccine for use according to the second aspect have an immunologically effective amount of *C. perfringens* Type A alpha toxoid from 0.1 to 100% (v/v), particularly from 0.5 to 50% (v/v), and more particularly from 1 to 25% (v/v). More in particular from 8 to 10% (v/v).

In another particular embodiment, optionally in combination with any embodiments above or below, the immunogenic composition for use according to the first aspect and the vaccine for use according to the second aspect have an immunologically effective titer of *C. perfringens* Type A alpha toxoid of at least 8.0 haemolytic titre (HA, $\log_2$HA50%/ml), titrated based on the haemolytic activity before the inactivation step. Particularly of at least 8.5, of at least 9.0, of at least 9.5, of at least 10.0, of at least 10.5, of at least 11.0, of at least 11.5, of at least 12.0, of at least 12.5, of at least 13.0, of at least 13.5, of at least 14.0, of at least 14.5, of at least 15.0, of at least 15.5, of at least 16.0, of at least 16.5, of at least 17.0, of at least 17.5 or of at least 18.0 HA. Preferably, between 8.0 and 18.0 HA, more preferably, between 11.0 and 17.5 HA. The HA assay is a routine method for the toxic effect titration. The details of the procedure are described below and are well-known by any person skilled in the art.

Particularly, in the immunogenic composition for use according to the first aspect and in the vaccine for use according to the second aspect, *C. difficile* toxoids A and B (TcdA/TcdB) and *C. perfringens* Type A alpha toxoid are present in a ratio from 0.1:99 to 99:0.1, preferably from 0.5:50 to 50:0.5, more preferably from 20:1 to 1:20 and more preferably from 10:2 to 2:10. More in particular 2:10.

In yet another embodiment, the immunogenic composition or the vaccine comprising it for use according to the first and second aspects further comprises one or more additional antigens, wherein the additional antigen is selected from a group of the microorganisms consisting of *Actinobacillus, Bordetella, Borrelia, Brachyspira, Brucella, Campylobacter, Chlamydia* and *Chlamydophila, Clostridium, Corynebacterium, Enterococcus, Erysipelothrix, Escherichia, Francisella, Haemophilus, Helicobacter, Isospora, Lawsonia, Legionella, Leptospira, Listeria, Mycobacterium, Mycoplasma, Neisseria, Pasteurella, Pseudomonas, Rickettsia, Salmonella, Shigella, Staphylococcus, Streptococcus, Treponema Vibrio* and, *Yersinia* genus, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED) and porcine circovirus and combinations thereof.

Particularly, the immunogenic composition or the vaccine comprising it for use according to the first and second aspects further comprises an antigen selected from the group consisting of *E. coli* F4ab, F4ac, F5 and F6 fimbrial adhesins; *E. coli* LT enterotoxoid, *C. perfringens* Type C toxoid; *C. novyi* Type B toxoid; and combinations thereof. Particularly, the immunogenic composition or the vaccine comprising it comprises the antigens *E. coli* F4ab, F4ac, F5 and F6 fimbrial adhesins; *E. coli* LT enterotoxoid, *C. perfringens* Type C toxoid; and *C. novyi* Type B toxoid. Particularly, the immunogenic composition of the invention further comprises the antigens of SUISENG®, RHINISENG®, ERYSENG®, ERYSENG® PARVO, ERYSENG® PARVO LEPTO, PARVOSENG®, VPURED® (Laboratorios HIPRA, S.A.). Thus, more particularly, the immunogenic composition and the vaccine for use as disclosed above for use in the prevention and/or treatment of enteric infections or diseases caused by a microorganism selected from *C. difficile* and *C. perfringens*, it is further for use in the prevention and/or treatment of infections or diseases caused by a microorganism selected from *Clostridium novyi*, *E. coli*, and mixtures thereof.

In another particular embodiment, the immunogenic composition according to the first aspect or the vaccine comprising it according to the second aspect are for use in a method for providing maternal passive immunization to the progeny of a livestock female, particularly by means of lactation.

Suitable carriers, excipients, etc. for preparing the vaccines for use according to the invention can be found in standard pharmaceutical texts, and include, as a way of example preservatives, agglutinants, humectants, emollients, and antioxidants.

In a particular embodiment, optionally in combination with any embodiment above or below, the pharmaceutically acceptable excipient comprises any pharmaceutically acceptable component other than the immunogenic component. The carrier can be organic, inorganic, or both. Suitable carriers well known to those of skill in the art and include, without limitation, large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles.

Additionally, if desired, the carrier can contain pharmaceutically acceptable auxiliary substances such as, for example, wetting agents, dispersing agents, emulsifying agents, buffering agents (for example, phosphate buffer), chelating agents (for example EDTA, citric acid, acetic acid), stabilizing agents such as carbohydrates (for example, glucose, sucrose, mannitol, sorbitol, starch, or dextrans), or proteins (for example, albumin, casein, bovine serum, or skimmed milk).

The compositions of the present invention for the proposed uses according to first and second aspects, can be prepared according to methods well known in the state of the art. The appropriate excipients and/or carriers, and their amounts, can readily be determined by those skilled in the art according to the type of composition being prepared.

Excipients usually used in vaccines include without any limitation any and all solvents, dispersion media, wetting agents, chelating agents, emulsifying agents, coatings, immunomodulators, immunostimulants, adjuvants, stabilizing agents such as carbohydrates (for example glucose, sucrose, mannitol, sorbitol, starch or dextrans), diluents, buffer agents (for example phosphate buffer), proteins (for example albumin, casein, bovine serum or skimmed milk), preservatives, isotonic agents, adsorption delaying agents, and the like. In preferred embodiments, especially those that include lyophilized immunogenic compositions, stabilizing agents for use in the present invention include stabilizers for lyophilization or freeze-drying. The physical-chemical characteristics of the excipients as well as the name of the commercial products under which they are marketed can be found in the book R. C. Rowe et al., Handbook of Pharmaceutical Excipients, $4^{th}$ edition, Pharmaceutical Press, London, 2003 [ISBN: 0-85369-472-9].

Adjuvants can also optionally be incorporated in the vaccine of the invention to enhance the effectiveness thereof. Alternatively, the adjuvant may be administered before, or after the administration of the vaccine of the invention.

Thus, in another embodiment, optionally in combination with any embodiment above or below, the vaccine for use according to the second aspect of the invention further comprises an adjuvant. The adjuvants, as is well known in the art, are nonspecific stimulants of the immune system, which, administered together with the antigen, enhance the immunological response. Particularly, adjuvants as used herein, can include aluminum hydroxide and aluminum phosphate, aluminum oxide, muramyl dipeptides, vitamin E, squalene, squalene, saponins for example Quil A, QS-21, ginseng, zymosan, glucans, non-ionic block polymers, monophosphoryl lipid A, vegetable oils, complete Freund's adjuvant, incomplete Freund's adjuvant, W/O, O/W, W/O/W type emulsions, Ribi adjuvant system (Ribi Inc.), heat-labile enterotoxin from *E. coli* (recombinant or otherwise), cholera toxin, dimethylaminoehtyldextran, dextrans or analogs or mixtures thereof. In a particular embodiment, the adjuvant comprises aluminum hydroxide, diethylaminoethyl dextran and *Ginseng*.

In another embodiment, the vaccine for use according to the second aspect of the invention is for preventing and/or treating *Clostridium* sp. enteric infections and/or disease in livestock. Particularly swine, wherein swine is selected from the group consisting of pigs, boars, sows, gilts and piglets. More particularly, is for providing maternal passive immunity to the progeny of a gilt or sow prior to the farrow, i.e., before parturition or given birth to the progeny.

In a particular embodiment, the vaccine for use according to the invention is for providing maternal passive immunity to the progeny (also known as offspring or litter) of a livestock female, particularly of a fertile and/or pregnant livestock female through lactation. More particularly, the maternal passive immunity or protection of the progeny relies upon the transfer of specific antibodies from the fertile and/or pregnant livestock female to their offspring in the form of colostral antibodies that will passively protect their litter.

As will be depicted in the examples below, immunization of females allowed passive immunization of their progeny, due to the fact that antibodies also detected in the serum and colostrum of the females passed through lactation and effectively reached the progeny. This allowed protection of progeny after challenge with *Clostridium* species.

In a more particular embodiment, the immunological composition or the vaccine of the present invention is for use in a method of providing maternal passive immunity against a clostridial disease to the progeny of a sow or gilt, or to the progeny of any livestock female, said method comprising administering an immunologically effective amount of the immunological composition, or the vaccine to the sow or gilt prior to the farrow (or to any livestock female); wherein the piglets (or progeny) are provided with maternal passive immunity, particularly through lactation. In still another particular embodiment, the clostridial diseases (or diseases caused by *Clostridium* sp.) are enteric infections and/or diseases. In still another particular embodiment, the *Clostridium* sp. is selected from *C. difficile*, *C. perfringens* and mixtures thereof, and the enteric infections or diseases are caused by these *Clostridium* species. In a still particular embodiment, the above method of providing maternal passive immunity, particularly by means of lactation, comprises the administration of at least two doses of the immunologically effective amount of the immunological composition or the vaccine of the invention to the livestock female.

Alternatively, this can be formulated as a method of providing maternal passive immunity to the progeny of a pregnant female livestock animal, particularly by means of lactation, against a disease caused by *Clostridium* sp., the method comprising administering an immunologically effective amount of the immunogenic composition or the vaccine of the present invention to the pregnant female livestock animal prior to the birth of the progeny. In a particular embodiment, the method comprises the administration of at least two doses of the immunologically effective amount of the immunological composition, or the vaccine of the invention to the pregnant female livestock animal. In another particular embodiment, the pregnant female livestock is swine. In still another particular embodiment, the diseases caused by *Clostridium* sp. are an enteric infections and/or diseases. In still another particular embodiment, the *Clostridium* sp. is selected from *C. difficile*, *C. perfringens* and mixtures thereof, and the enteric infections or diseases are caused by these *Clostridium* species. More particularly, the *Clostridium* sp. is selected from *C. difficile, C. perfringens* Type A and mixtures thereof, and the enteric infections or diseases are caused by these *Clostridium* species.

Also alternatively, this can be formulated as the use of the immunologically effective amount of the immunogenic composition or the vaccine of the invention as defined above for the manufacture of a medicament for the provision of maternal passive immunity against enteric infections or diseases caused by *Clostridium* sp. More in particular, the *Clostridium* sp. is selected from *C. difficile, C. perfringens* and mixtures thereof, and the enteric infections or diseases are caused by these *Clostridium* species. More particularly, the *Clostridium* sp. is selected from *C. difficile, C. perfringens* Type A and mixtures thereof, and the enteric infections or diseases are caused by these *Clostridium* species. The vaccines of the invention are typically prepared as parenteral vaccines in the form of solutions, emulsions or liquid suspensions. They can also be prepared in a solid form suitable to be dissolved or suspended in a liquid vehicle before injection.

Particularly, the vaccine of the invention is (a) in liquid form; or (b) in dry powder form, lyophilized, freeze dried, spray dried, or foam dried.

The typical volume of a dose of an injection vaccine of the invention is between 0.1 ml and 5 ml, particularly between 0.15 ml and 3 ml, and more particularly between 0.2 ml and 2 ml. Usually, for intramuscular administration it is used between 0.5 ml and 5 ml, particularly between 1 ml and 3 ml, and more particularly between 1 ml and 2 ml.

The liquid vehicles which can be used for preparing the vaccine of the invention include, for example, water (in particular, water for injection), saline solution with a physiological salt concentration, or the culture liquid in which the bacteria are cultured.

The immunological composition of the first aspect of the invention or the vaccine of the second aspect of the invention can be administered by different routes of administration. Particular routes include but are not limited to oral, transdermal, transmucosal (i.e. mucosally and/or submucosally), intradermal, subcutaneous, intramuscular, intranasal, by means of aerosol, intraperitoneal or intravenous route. Particularly they are administered by intramuscular route. According to the desired duration and effectiveness of the treatment, the compositions and vaccines according to the invention may be administered once or several times, also intermittently, for example on a daily basis for several days, weeks or months and/or in different dosages. The timing of doses depends upon factors well known in the art. After the initial administration, one or more additional doses may be administered to maintain and/or boost the effectiveness of the initial doses. Particularly, the immunogenic compositions or the vaccines of the invention are administered several times. More particularly the vaccination plan comprises two doses administered before farrowing, the first dose administered at approximately 6 weeks before farrowing and the second dose at approximately 3 weeks before farrowing. In one embodiment, when the vaccination plan of two doses has been given to an animal for the first time, then only a single dose is necessary at the following farrowing. Therefore, the immunogenic compositions or the vaccines of the invention may also be administered at a single dose. The vaccine of the invention can be prepared according to the standard process used by the person skilled in the art for the preparation of pharmaceutical formulations suitable for the different forms of administration as is described for example in the manual Remington The Science and Practice of Pharmacy, 20$^{th}$ edition, Lippincott Williams & Wilkins, Philadelphia, 2000 [ISBN: 0-683-306472]. More particularly, the vaccine is for use by intramuscular route.

As exposed above, a third aspect of the invention is related to an immunogenic composition comprising, (a) one or more *C. difficile* toxoids selected from the group consisting of *C. difficile* A toxoid, *C. difficile* B toxoid, and mixtures thereof; and (b) one or more *C. perfringens* Type A toxoid.

One embodiment of the third aspect of the invention is related to an immunogenic composition comprising, (a) one or more a *C. difficile* toxoid selected from the group consisting of *C. difficile* A toxoid, *C. difficile* B toxoid and mixtures thereof; and further comprising *C. difficile* Binary toxoid (CDT); and (b) one or more a *C. perfringens* Type A toxoid.

One embodiment of the third aspect of the invention is related to an immunogenic composition comprising, (a) one or more a *C. difficile* toxoid selected from the group consisting of *C. difficile* A toxoid, *C. difficile* B toxoid and mixtures thereof, and optionally further comprising *C. difficile* Binary toxoid (CDT); and (b) one or more a *C. perfringens* Type A alpha toxoid.

Another embodiment of the third aspect comprises a *C. difficile* A toxoid, a *C. difficile* B toxoid, and a *C. perfringens* Type A alpha toxoid. More particularly, the *C. difficile* A toxoid is derived from a *C. difficile* A toxin which comprises SEQ ID NO: 1, or a sequence that has at least a 80% sequence identity with SEQ ID NO: 1. Yet more particularly, the *C. difficile* A toxin comprises SEQ ID NO: 1, and yet more particularly, the *C. difficile* A toxin consists of SEQ ID NO: 1. Also more particularly, the immunogenic composition comprises the *C. difficile* B toxoid which is derived from a *C. difficile* B toxin which comprises SEQ ID NO: 2, or a sequence that has at least a 80% sequence identity with SEQ ID NO: 2. Yet more particularly, the *C. difficile* B toxin comprises SEQ ID NO: 2, and yet more particularly, the *C. difficile* B toxin consists of SEQ ID NO: 2.

In another particular embodiment, the *C. difficile* A toxoid is derived from a *C. difficile* A toxin that has a sequence identity of 80%, 81%, 82%, 83%, 84%, 85%, 86%, 87%, 88%, 89%, 90%, 91%, 92%, 93%, 94%, 95%, 96%, 97%, 98% or 99% with SEQ ID NO: 1.

In another particular embodiment, the *C. difficile* B toxoid is derived from a *C. difficile* B toxin that has a sequence identity of 80%, 81%, 82%, 83%, 84%, 85%, 86%, 87%, 88%, 89%, 90%, 91%, 92%, 93%, 94%, 95%, 96%, 97%, 98% or 99% with SEQ ID NO: 2.

Another particular embodiment of the third aspect, optionally in combination with the embodiments above or below, the immunogenic composition comprises the *C. perfringens* Type A alpha toxoid which is derived from a *C. perfringens* Type A alpha toxin which comprises SEQ ID NO: 3, or a sequence that has at least a 80% sequence identity with SEQ ID NO: 3. Yet more particularly, the *C. perfringens* Type A alpha toxin comprises SEQ ID NO: 3, and yet more particularly, the *C. perfringens* alpha toxin consists of SEQ ID NO: 3.

In another particular embodiment, the *C. perfringens* Type A alpha toxoid is derived from a *C. perfringens* Type A alpha toxin that has a sequence identity of 80%, 81%, 82%, 83%, 84%, 85%, 86%, 87%, 88%, 89%, 90%, 91%, 92%, 93%, 94%, 95%, 96%, 97%, 98% or 99% with SEQ ID NO: 3.

Yet in another embodiment, optionally in combination with any embodiment above or below, these new immunogenic compositions of the invention further comprise one or more additional antigens, wherein the additional antigen is selected from a group of the microorganisms consisting of *Actinobacillus, Bordetella, Borrelia, Brachyspira, Brucella, Campylobacter, Chlamydia* and *Chlamydophila, Clostridium, Corynebacterium, Enterococcus, Erysipelothrix, Escherichia, Francisella, Haemophilus, Helicobacter, Isospora, Lawsonia, Legionella, Leptospira, Listeria, Mycobacterium, Mycoplasma, Neisseria, Pasteurella, Pseudomonas, Rickettsia, Salmonella, Shigella, Staphylococcus, Streptococcus, Treponema Vibrio* and *Yersinia* genus, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED) and porcine circovirus and combinations thereof.

More particularly, the additional antigens are selected from the group consisting of *E. coli* F4ab, F4ac, F5 and F6 fimbrial adhesins; *E. coli* LT enterotoxoid, *C. perfringens* Type C toxoid; *C. novyi* Type B toxoid; and combinations thereof. Particularly, the immunogenic composition or the vaccine comprising it comprises the antigens *E. coli* F4ab, F4ac, F5 and F6 fimbrial adhesins; *E. coli* LT enterotoxoid, *C. perfringens* Type C toxoid; and *C. novyi* Type B toxoid. Particularly, the immunogenic composition of the invention further comprises the antigens of SUISENG®, RHINISENG®, ERYSENG®, ERYSENG® PARVO, ERYSENG® PARVO LEPTO, PARVOSENG®, VPURED® (Laboratorios HIPRA, S.A.).

The toxoids can be obtained as described above and can be contained in a whole cell preparation, in a cell-free preparation (supernatants) or even as completely purified proteins, which means that the toxoids have been isolated from said supernatants and the final composition comprises a solvent and the toxoid. Methods for totally purifying the proteins are those known for the skilled man including, for example, size exclusion chromatography, SDS-PAGE (sodium dodecyl sulfate-polyacrylamide gel electrophoresis) or by high performance liquid chromatography or reversed-phase chromatography, or by dialysis, among others.

In another particular embodiment, optionally in combination with any embodiment above or below, the immunogenic composition according to the third aspect has an immunologically effective amount of *C. difficile* A toxoid from 0.1 to 100% (v/v), particularly from 0.5 to 50% (v/v), and more particularly from 1 to 25% (v/v), even more in particular from 1 to 10% (v/v).

In another particular embodiment, optionally in combination with any embodiment above or below, the immunogenic composition according to the third aspect has an immunologically effective amount of *C. difficile* B toxoid from 0.1 to 100% (v/v), particularly from 0.5 to 50% (v/v), and more particularly from 1 to 25% (v/v), even more in particular from 1 to 10% (v/v).

In another particular embodiment, optionally in combination with any embodiment above or below, the immunogenic composition according to the third aspect has an immunologically effective titer of *C. difficile* toxoids A and B (TcdA/TcdB) of at least 5.0 cytopathic titre (CPE, $\log_{10}$CPE/ml), titrated based on the cytopathic effect before the inactivation step. Particularly of at least 5.5, of at least 6.0, of at least 6.5, of at least 7.0, of at least 7.5, of at least 8.0, of at least 8.5, of at least 9.0, of at least 9.5, of at least 10.0, of at least 10.5, or of at least 11.0 CPE. Preferably, between 5.0 and 11.0 CPE, more preferably, between 6.5 and 9.5 CPE. The CPE assay is a routine method for the toxic effect titration. The details of the procedure are described below and are well-known by any person skilled in the art.

In yet another particular embodiment, optionally in combination with any embodiment above or below, the immunogenic composition according to the third aspect, the *C. difficile* toxoids A and B (TcdA/TcdB) are present in a ratio from 99:0.1 to 0.1:99, preferably from 50:0.5 to 0.5:50, more preferably from 10:1 to 1:10, more preferably from 5:1 to 1:5, more preferably from 2.5:1 to 1:2.5 and more preferably 2.5:1.

In yet another particular embodiment, optionally in combination with any embodiment above or below, the immunogenic composition according to the third aspect has an immunologically effective amount of *C. perfringens* Type A alpha toxoid from 0.1 to 100% (v/v), preferably from 0.5 to 50% (v/v), and more preferably from 1 to 25% (v/v). Even more preferably from 8 to 10% (v/v).

In another particular embodiment, optionally in combination with any embodiment above or below, the immunogenic composition according to the third aspect has an immunologically effective titer of *C. perfringens* Type A alpha toxoid of at least 8.0 haemolytic titre (HA, $\log_2$HA50%/ml), titrated based on the haemolytic activity before the inactivation step. Particularly, of at least 8.5, of at least 9.0, of at least 9.5, of at least 10.0, of at least 10.5, of at least 11.0, of at least 11.5, of at least 12.0, of at least 12.5, of at least 13.0, of at least 13.5, of at least 14.0, of at least 14.5, of at least 15.0, of at least 15.5, of at least 16.0, of at least 16.5, of at least 17.0, of at least 17.5 or of at least 18.0 HA. Preferably, between 8.0 and 18.0 HA, more preferably, between 11.0 and 17.5 HA. The HA assay is a routine method for the toxic effect titration. The details of the procedure are described below and are well-known by any person skilled in the art.

Particularly, in the immunogenic composition according to the third aspect of the invention, the *C. difficile* A (TcdA)/B (TcdB) toxoid and *C. perfringens* Type A alpha toxoid are present in a ratio from 0.1:99 to 99:0.1, preferably from 0.5:50 to 50:0.5, more preferably from 20:1 to 1:20 and more preferably from 10:2 to 2:10. Even more preferably 2:10.

As described above, a fourth aspect of the invention also relates to a vaccine comprising the immunogenic composition of the third aspect of the invention and a pharmaceutically acceptable excipient and/or carrier. All particular embodiments of the immunogenic composition according to the third aspect of the invention, also apply to the vaccine of the fourth aspect of the invention.

In a particular embodiment, the vaccine of the invention further comprises an adjuvant.

The excipients, carriers and adjuvants that may be comprised in the vaccine of the fourth aspect of the invention have been described above. As well as the route of administration and the vaccination plan. Particular routes include but are not limited to oral, transdermal, transmucosal (i.e. mucosally and/or submucosally), intradermal, subcutaneous, intramuscular, intranasal, by means of aerosol, intraperitoneal or intravenous route. Particularly they are administered by intramuscular route. According to the desired duration and effectiveness of the treatment, the compositions according to the invention may be administered once or several times, also intermittently, for example on a daily basis for several days, weeks or months and/or in different dosages. The timing of doses depends upon factors well known in the art. After the initial administration, one or more additional doses may be administered to maintain and/or boost the effectiveness of the initial doses. Particularly, the immunogenic compositions or the vaccines of the invention are administered several times. More particularly the vaccination plan comprises two doses administered before farrowing, the first dose administered at approximately 6 weeks before farrowing and the second dose at approximately 3 weeks before farrowing. In one embodiment, when the vaccination plan of two doses has been given to an animal for the first time, then only a single dose is necessary at the following farrowing.

Therefore, the immunogenic compositions or the vaccines of the invention may also be administered at a single dose. The vaccine of the invention can be prepared according to the normal process used by the person skilled in the art for the preparation of pharmaceutical formulations suitable for the different forms of administration as is described for example in the manual Remington The Science and Practice of Pharmacy, 20$^{th}$ edition, Lippincott Williams & Wilkins, Philadelphia, 2000 [ISBN: 0-683-306472]. More particularly, the vaccine is for use by intramuscular route.

The immunogenic composition according to the third aspect of the invention, as well as any vaccine comprising it, as disclosed for the fourth aspect, is for use as a medicament. More in particular for preventing and/or treating enteric infections or disease in a subject. Thus, it can be administered in a subject in need thereof in an immunologically effective amount in a method for preventing and/or treating enteric infections or diseases caused by *Clostridium* sp. That is, the immunogenic composition or the vaccine as defined above are for the manufacture of a medicament for the treatment and/or prevention of enteric infections or diseases caused by *Clostridium* sp. More in particular, the *Clostridium* sp. is selected from *C. difficile, C. perfringens* and mixtures thereof, and the enteric infections or diseases are caused by these *Clostridium* species. More particularly, the *Clostridium* sp. is selected from *C. difficile, C. perfringens* Type A and mixtures thereof, and the enteric infections or diseases are caused by these *Clostridium* species. In a particular embodiment, the vaccine for use according to the fourth aspect of the invention is for preventing and/or treating *Clostridium* sp. enteric infections and/or diseases in livestock. Particularly swine, wherein swine is selected from the group consisting of pigs, boars, sows, gilts and piglets. More particularly, is for providing maternal passive immunity to the progeny of a gilt or sow prior to the farrow, i.e., before parturition o given birth to the progeny, particularly by means of lactation.

In a fifth aspect of the invention, the immunogenic composition or the vaccine comprising it, as defined or according to any of the previous aspects of the invention, are for use as a medicament, which is for use in a method for providing maternal passive immunization to the progeny of a livestock female, particularly by means of lactation, the method comprising administering the immunogenic composition or the vaccine to the pregnant female livestock animal prior to the birth of the progeny. Particularly, the passive immunity or protection of the progeny relies upon the transfer of specific maternal antibodies from the fertile and/or pregnant livestock female to their offspring in the form of colostral antibodies that will passively protect their litter.

As will be shown in the examples below, immunization of females allowed maternal passive immunization of their progeny, due to the fact that antibodies also detected in the serum and colostrum of the females passed through lactation and effectively reached the progeny. This allowed protection of progeny after challenge with *Clostridium* species.

In a more particular embodiment of the fifth aspect of the invention, is for use in a method of providing maternal passive immunity against a clostridial disease to the progeny of a sow or gilt, or to the progeny of any livestock female, said method comprising administering an immunologically effective amount of the immunological composition, or the vaccine to the sow or gilt prior to the farrow (or to any livestock female), wherein the piglets (or progeny) are provided with maternal passive immunity, particularly through lactation. In still another particular embodiment, the diseases caused by *Clostridium* sp. are enteric infections and/or diseases. In still another particular embodiment, the *Clostridium* sp. is selected from *C. difficile, C. perfringens* and mixtures thereof, and the enteric infections or diseases are caused by these *Clostridium* species. In a still particular embodiment, the above method of providing maternal passive immunity, particularly by means of lactation, comprises the administration of at least two doses of the immunologically effective amount of the immunological composition, or the vaccine of the invention to the livestock female.

Alternatively, the above can be formulated as a method of providing maternal passive immunity to the progeny of a pregnant female livestock animal, particularly by means of lactation, against diseases caused by *Clostridium* sp., the method comprising administering an immunologically effective amount of the immunogenic composition or the vaccine comprising it, to the pregnant female livestock animal prior to the birth of the progeny. In a particular embodiment, the method comprises the administration of at least two doses to the pregnant female livestock animal. In another particular embodiment, the pregnant female livestock is swine. In still another particular embodiment, the disease caused by *Clostridium* sp. is enteric infections and/or diseases. In still another particular embodiment, the *Clostridium* sp. is selected from *C. difficile, C. perfringens* and mixtures thereof, and the enteric infections or diseases are caused by these *Clostridium* species.

Also alternatively, this can be formulated as the use of an immunologically effective amount of the immunogenic composition or the vaccine comprising it, for the manufacture of a medicament for the provision of maternal passive immunity against enteric infections or diseases caused by *Clostridium* sp. More in particular, the *Clostridium* sp. is selected from *C. difficile, C. perfringens* and mixtures thereof, and the enteric infections or diseases are caused by these *Clostridium* species. More particularly, the *Clostridium* sp. is selected from *C. difficile, C. perfringens* Type A and mixtures thereof, and the enteric infections or diseases are caused by these *Clostridium* species.

As exposed before, a seventh aspect of the invention is a vaccination kit comprising:
(a) an immunogenic composition as defined above according to the third aspect;
(b) a pharmaceutically acceptable excipient and/or carrier;
(c) optionally an adjuvant; and
(d) optionally instructions for its use.

This vaccination kit as defined above is, in particular, for use in the prevention and/or treatment of a disease caused by *Clostridium* sp. Additionally, the vaccination kit may also be a vaccination kit-of-parts.

Other vaccination kits for vaccinating a subject against an infection or disease caused by *Clostridium* sp. are also part of the invention. In particular, those comprising the vaccine of the fourth aspect of the invention and further immunologic compositions and/or vaccines against another disease or pathological conditions caused by microorganisms. In particular, are also part of the invention those kits comprising one or more vials with the immunogenic compositions of the invention, and/or the vaccines comprising them, and optionally other vaccines against other diseases, together with instructions (such as a leaflet) with the indication for use in the prevention and/or treatment of the diseases, in particular those diseases caused by *C. difficile* in livestock and other diseases when combined with the vaccine of the invention. The vaccination kits may also contain in addition another container containing an aqueous solution for reconstituting the final composition to be administered. The vaccination kit may optionally include one or more (medical) devices for the administration. In another particular embodiment, the vaccination kit is for use in diseases caused by *C. difficile* and *C. perfringens* in livestock. In another particular embodiment, the vaccination kit is for use in enteric infections or diseases caused by *C. difficile*, *C. perfringens* and mixtures thereof.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

FURTHER EMBODIMENTS

The present invention also provides the following embodiments as defined in items 1 to 27 below:
1. An immunogenic composition comprising one or more *Clostridium difficile* (*C. difficile*) toxoid for use as a medicament in livestock.
2. The immunogenic composition for use according to item 1, wherein the livestock is swine.
3. The immunogenic composition for use according to any one of items 1 to 2, which is for use in the prevention and/or treatment of a disease caused by *Clostridium* sp.
4. The immunogenic composition for use according to any one of items 1 to 3, which is for preventing and/or treating *Clostridium* sp. enteric infections and/or disease.
5. The immunogenic composition for use according to any one of items 1 to 4, wherein the toxoid is selected from the group consisting of *C. difficile* A toxoid, *C. difficile* B toxoid, *C. difficile* Binary toxoid, and mixtures thereof.
6. The immunogenic composition for use according to any one of items 1 to 5, comprising a *C. difficile* A toxoid and a *C. difficile* B toxoid.
7. The immunogenic composition for use according to any one of items 1 to 6, further comprising one or more *Clostridium perfringens* (*C. perfringens*) toxoid.
8. The immunogenic composition for use according to item 7, wherein the one or more *C. perfringens* toxoid is a *C. perfringens* Type A alpha toxoid.
9. The immunogenic composition for use according to any one of items 1 to 8, further comprising one or more additional antigens, wherein the additional antigen is selected from a group of microorganisms consisting of *Actinobacillus, Bordetella, Borrelia, Brachyspira, Brucella, Campylobacter, Chlamydia* and *Chlamydophila, Clostridium, Corynebacterium, Enterococcus, Erysipelothrix, Escherichia, Francisella, Haemophilus, Helicobacter, Isospora, Lawsonia, Legionella, Leptospira, Listeria, Mycobacterium, Mycoplasma, Neisseria, Pasteurella, Pseudomonas, Rickettsia, Salmonella, Shigella, Staphylococcus, Streptococcus, Treponema Vibrio* and *Yersinia* genus, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED) porcine circovirus, and combinations thereof.
10. The immunogenic composition for use according to item 9, wherein the one or more additional antigens are selected from the group consisting of *E. coli* F4ab, F4ac, F5 and F6 fimbrial adhesins; *E. coli* LT enterotoxoid; *C. perfringens* Type C toxoid; *C. novyi* Type B toxoid; and combinations thereof.
11. The immunogenic composition for use according to any one of items 1 to 10, which is for use in a method for providing maternal passive immunization to the progeny of a livestock female, optionally by means of lactation.
12. A vaccine for use as a medicament in livestock comprising:
(a) an immunogenic composition comprising one or more *C. difficile* toxoids as defined in any of items 1-10; and
(b) a pharmaceutically acceptable excipient and/or carrier.
13. The vaccine for use according to item 12, further comprising and adjuvant.
14. The vaccine for use according to any one of items 12 to 13, which is for providing maternal passive immunity to the progeny of a livestock female, optionally by means of lactation.
15. The vaccine for use according to any one of items 12 to 14 or the immunogenic composition for use according to any one of items 1 to 11, which is for use intranasally, intradermally, transmucosally (mucosally and/or submucosally), subcutaneously, by means of aerosol, intramuscularly, intravenously, or orally.
16. An immunogenic composition comprising:
(a) one or more *C. difficile* toxoids selected from the group consisting of a *C. difficile* A toxoid (TcdA), a *C. difficile* B toxoid (TcdB), and mixtures thereof; and
(b) one or more *C. perfringens* Type A toxoid.
17. The immunogenic composition according to item 16, comprising a *C. difficile* A toxoid, a *C. difficile* B toxoid, and a *C. perfringens* Type A alpha toxoid,
18. The immunogenic composition according to any one of items 16 to 17, further comprising one or more additional antigens, wherein the additional antigen is selected from a group of microorganisms consisting of *Actinobacillus, Bordetella, Borrelia, Brachyspira, Brucella, Campylobacter, Chlamydia* and *Chlamydophila, Clostridium, Corynebacterium, Enterococcus, Erysipelothrix, Escherichia, Francisella, Haemophilus, Helicobacter, Isospora, Lawsonia, Legionella, Leptospira, Listeria, Mycobacterium, Mycoplasma, Neisseria, Pasteurella, Pseudomonas, Rickettsia, Salmonella, Shigella, Staphylococcus, Streptococcus, Treponema Vibrio* and *Yersinia* genus, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED), porcine circovirus and combinations thereof.

19. The immunogenic composition according to item 18, wherein the one or more additional antigens are selected from the group consisting of *E. coli* F4ab, F4ac, F5 and F6 fimbrial adhesins, *E. coli* LT enterotoxoid, *C. perfringens* Type C toxoid, *C. novyi* Type B toxoid, and combinations thereof.

20. A vaccine comprising the immunogenic composition as defined in any one of items 16 to 19 and a pharmaceutically acceptable excipient and/or carrier.

21. The vaccine according to item 20, further comprising an adjuvant.

22. A process for making the vaccine according to any one of items 20 to 21, which comprises the step of mixing the immunogenic composition as defined in any one of items 16 to 19 with a pharmaceutically acceptable excipient and/or carrier.

23. A vaccination kit comprising:
(a) an immunogenic composition as defined in any of items 16 to 19;
(b) a pharmaceutically acceptable excipient and/or carrier;
(c) optionally an adjuvant; and
(d) optionally instructions for its use.

24. The vaccination kit as defined in item 23 for use in the prevention and/or treatment of a disease caused by *Clostridium* sp., optionally *Clostridium* sp. enteric infection and/or disease, wherein the *Clostridium* sp. is selected from *C. difficile*, *C. perfringens*, and mixtures thereof.

25. The immunogenic composition for use according to any one of items 1 to 10, the immunogenic composition as defined in any one of items 16 to 19, the vaccine for use according to any one of items 12 to 15, and the vaccine as defined in any of items 20 to 21, which is for use in a method of providing maternal passive immunity to the progeny of a livestock female, optionally by means of lactation, the method comprising administering the immunogenic composition or the vaccine to the pregnant female livestock animal prior to the birth of the progeny.

26. The immunogenic composition or the vaccine for use according to item 25, wherein the method of providing maternal passive immunity comprises the administration of at least two doses to the pregnant female livestock animal.

27. The immunogenic composition or the vaccine for use according to any one of items 25 to 26, which is for use intranasally, intradermally, transmucosally (mucosally and/or submucosally), subcutaneously, by means of aerosol, intramuscularly, intravenously, or orally.

EXAMPLES

Example 1: Production of the Vaccine of the Invention

Different vaccine compositions were prepared. Before formulating the vaccine compositions, the inactivated toxins, i.e. the toxoids, were obtained as described below.

1.1. Production of *C. difficile* Inactivated TcdA and TcdB Toxins

*C. difficile* strain B-7727 was used to obtain the TcdA and TcdB toxins. This strain is a field isolate from Laboratorios HIPRA, S.A. and it produces both TcdA and TcdB toxins. Colonies of *C. difficile* were inoculated into 10 ml containing 36 g/L of BHI (Brain Heart Infusion, Becton Dickinson #237500) broth supplemented with 0.5% yeast extract (Becton Dickinson #212750) and 0.05% L-cystine (Amresco #0206) in a 20×150 mm Hungate tube, under an atmosphere of 5% $CO_2$:5% $H_2$:90% $N_2$ and incubated at 37° C. overnight. An amount of 1-2 ml of this overnight culture was used to inoculate a loop of dialysis tubing (MW cutoff 10 kDA, SpectrumLabs #132129) suspended in a 4 L erlenmeyer flask containing 4 L of BHI broth supplemented with 0.5% yeast extract and 0.05% L-cystine. The flask was incubated at 37° C. in an anaerobic incubator. After 5-7 days, the material in the dialysis tubing was collected and the supernatant was clarified by centrifugation (15,000×g, 20 minutes) and sterilized by filtration with a pore diameter of 0.22 μm. After the sterilizing filtration, a solution of formaldehyde was added to a final concentration of 0.8% w/v and maintained during 6 days at 37° C. with stirring in order to inactivate the supernatant. Finally, a dialysis was performed with PBS to remove residual formaldehyde.

Supernatant containing the purified TcdA and TcdB toxoids was then stored at 4° C. for the future preparation of the vaccine. Quantification of TcdA/TcdB toxins was done by assaying its cytopathic effect (CPE) before the inactivation step. For the activity assay, African green monkey kidney (Vero) cells were used as follows: $10^5$ Vero cells/ml were seeded at in 96-well tissue culture plates in 100 μl of sterile Glasgow MEM (ThermoFisher) containing 10% (v/v) fetal bovine serum and incubated 3-4 hours to allow the adhesion of cells. Serial 10-fold dilutions of culture filtrates were prepared in duplicate in sterile Glasgow MEM+10% FBS and 10 μl were added to the Vero cells. Control wells were dispensed with the diluent alone. Plates were incubated for 4 days (37° C. and 5% CO2), stained with crystal violet using standard procedures and the optical density (OD) was measured with a 96-well plate reader at 595 nm. The cytotoxicity titer was defined as the reciprocal of the sample dilution that gave 50% of cell toxicity (CPE; $\log_{10}$CPE/ml). The ratio TcdA:TcdB in the supernatant was approximately 2.5:1.

1.2. Production of *C. perfringens* Type A Inactivated Alpha-Toxin

*C. perfringens* Type A strain 4476 was used to produce the alpha toxin. This strain is a field isolate from Laboratorios HIPRA, S.A. *C. perfringens* Type A culture was grown under anaerobic conditions in Cooked Meat Medium (Becton Dickinson #226730) prepared following the fabricant instructions. It was cultured under strict anaerobiosis conditions at 37° C. and about 4-5 hours. The supernatant was clarified by centrifugation (15,000×g, 20 minutes) to separate the *C. perfringens* Type A cells (pellet) and sterilized by filtration with a pore diameter of 0.22 μm. A formaldehyde and glycine solution was added to the supernatant to a final concentration of 0.8% w/v to inactivate the culture. The supernatant was maintained 8 days at 4° C. with stirring. Once the inactivation was completed, the resulting supernatant was concentrated using ultrafiltration with pore size of 10 kDa, followed by a diafiltration step with PBS. After the concentration, a final step of sterilizing filtration was done. The concentrated supernatant containing the purified alpha toxoid was then stored at 4° C. for the future preparation of the vaccine.

Quantification of the toxins was performed by assaying its haemolytic activity (HA) before the inactivation step as follows: Haemolytic activity was determined by using freshly drawn washed mouse erythrocytes suspended in PBS at 0.5%. Volumes (0.1 ml) of erythrocyte suspension were added to equal volumes of serial 2-fold dilutions of toxin in saline solution 0.9%. After incubation for 1 h at 37° C., the plate was centrifuged and the optical density (OD) of the supernatant was measured at 405 nm. The haemolytic titre (HA, $\log_2 HA_{50\%}$/ml) was defined as the reciprocal of the sample dilution that gave 50% of cell haemolysis.

The toxoids of the invention can also be obtained from alternative methodologies such as synthetic methodologies, for example by chemical synthesis of fragments and further linking to obtain the entire sequence of the toxoid. They can also be obtained by means of DNA recombinant technologies, as recombinant peptides produced in bacteria or in yeast. The skilled man being aware of these alternative methods and will recognize that although the toxins in the vaccine or the immunogenic composition of the invention may have the sequences selected from SEQ ID NO: 1, 2 and 3, or a sequence that has at least a 80% sequence identity with SEQ ID NO: 1, 2 and 3, they will also be effective in terms of eliciting the immune response when obtained by alternative methods other than those described in the Example 1.

1.3. Vaccine Compositions

Different vaccine compositions and containing different titres of the toxoids of the invention were prepared as follows:

1.3.1. Vaccine A: *C. difficile* Toxoid Formulations

*C. difficile* TcdA and TcdB toxoids obtained according to an analogous procedure as the one described in section 1.1. were titrated based on the cytopathic effect (CPE; $\log_{10}$CPE/ml) obtained prior to the inactivation. Vaccine A was formulated to obtain a titre of 9.4 CPE. The ratio of TcdA/TcdB toxoid was 2.5:1.

Vaccine A was formulated as follows: 25% (v/v) of TcdA/TcdB toxoid (antigenic phase) was mixed with PBS and 5% (w/v) of a ginseng solution at 4% (w/v), the solution was then homogenized. 25% (w/v) of an aluminum hydroxide gel was afterwards added and the volume was adjusted with PBS until the 100% of the volume was achieved obtaining a suspension for injection. Lastly, the pH of the vaccine formulation was adjusted to 7.4-7.8.

This vaccine formulation A was subsequently used in Example 2.

1.3.2. Vaccine B: *C. difficile* Toxoid Formulations

*C. difficile* TcdA/TcdB toxoid obtained according to an analogous procedure as the one described in section 1.1. was titrated based on the cytopathic effect (CPE; $\log_{10}$CPE/ml) obtained previous to the inactivation and diluted 10 times, in order to obtain Vaccine B with a titre of 8.4 CPE. The ratio of TcdA/TcdB toxoid was 2.5:1.

Vaccine B was formulated as follows: 2.5% (v/v) of TcdA/TcdB toxoid (antigenic phase) was then mixed with PBS and 5% (w/v) of a ginseng solution at 4% (w/v), the solution was then homogenized. 25% (w/v) of an aluminum hydroxide gel was afterwards added and the volume was adjusted with PBS until the 100% of the volume was achieved obtaining a suspension for injection. Lastly, the pH of the vaccine formulation was adjusted to 7.4-7.8.

This vaccine formulation B was subsequently used in Example 2

1.3.3. Vaccine 1: *C. difficile* Toxoid Formulations Combined with *C. perfringens* Type A Alpha-Toxoid and Other Antigens.

*C. difficile* TcdA/TcdB toxoid obtained according to an analogous procedure as the one described in section 1.1. was titrated based on the cytopathic effect (CPE; $\log_{10}$CPE/ml) obtained previous to the inactivation and diluted until achieve a titre of 8.8 CPE to formulate Vaccine 1. The ration of TcdA/TcdB toxoid was 2.5:1.

*C. perfringens* Type A alpha toxoid obtained according to an analogous procedure as the one described in section 1.2. was titrated based on the haemolytic activity (HA, $\log_2$HA$_{50\%}$/ml) obtained prior to the inactivation. Vaccine 1 was prepared to obtain a titre of 14.5 HA of *C. perfringens* Type A alpha toxoid.

Vaccine 1 was formulated in the same way as vaccine A. In this case, the antigenic phase contained: 25% (v/v) of TcdA/TcdB *C. difficile* toxoid and 25% (v/v) of *C. perfringens* Type A alpha toxoid. *C. difficile* TcdA/TcdB toxoid and *C. perfringens* Type A alpha toxoid were present in a ratio of 1:1. The antigenic phase was mixed with 2% (w/v) DEAE-Dextran and with a 10% (w/v) solution of ginseng at 4% (w/v) and 30% (w/v) aluminum hydroxide gel.

The formulation was homogenized and the suspension for injection was completed with PBS until the 100% of the volume was achieved. The pH was finally adjusted to 7.4-7.8.

Other Antigens:

The suspension for injection previously obtained was then mixed at 1:1 ratio with SUISENG® (LABORATORIOS HIPRA, S.A.). SUISENG® is a commercial vaccine against neonatal porcine colibacillosis and clostridiosis, which contains the following antigens: F4ab, F4ac, F5 and F6 fimbrial adhesins and LT enterotoxoid of *E. coli*, *C. perfringens* Type C toxoid and *C. novyi* Type B toxoid.

The vaccine formulation 1 in combination with SUISENG® was subsequently used in Example 3.

1.3.4. Vaccine 2: *C. difficile* Toxoid Formulations Combined with *C. perfringens* Type A Alpha-Toxoid and Other Antigens

*C. difficile* Antigens:

*C. difficile* TcdA/TcdB toxoid obtained according to an analogous procedure as the one described in section 1.1. was titrated based on the cytopathic effect (CPE; log 10CPE/ml) obtained prior to the inactivation and diluted to achieve a titre of 8.5 CPE to formulate Vaccine 2. The ratio of TcdA/TcdB toxoid was 2.5:1.

*C. perfringens* Antigens:

*C. perfringens* Type A alpha toxoid obtained according to an analogous procedure as the one described in section 1.2. was titrated based on the haemolytic activity (HA, $\log_2$HA$_{50\%}$/ml) obtained previous to the inactivation and diluted to achieve a titre of 13.5 HA of *C. perfringens* Type A alpha toxoid to formulate Vaccine 2.

Vaccine 2 was formulated as vaccine 1. In this case, the antigenic phase contained 12.5% (v/v) of *C. difficile* TcdA/TcdB toxoid and 12.5% (v/v) of *C. perfringens* Type A alpha toxoid, which corresponds to a ratio of *C. difficile* TcdA/TcdB toxoid and *C. perfringens* Type A alpha toxoid of 1:1. The mixture was homogenized with 2% (w/v) DEAE-Dextran, 10% (w/v) ginseng solution at 4% (w/v) and 30% (w/v) aluminum hydroxide gel. The suspension for injection obtained was completed with PBS until the 100% of the volume was achieved and the pH was finally adjusted to 7.4-7.8.

Other Antigens:

The suspension for injection previously obtained was then mixed at 1:1 ratio with SUISENG® (LABORATORIOS HIPRA, S.A.). SUISENG® is a commercial vaccine against neonatal porcine colibacillosis and clostridiosis, which contains the following antigens: F4ab, F4ac, F5 and F6 fimbrial adhesins and LT enterotoxoid of *E. coli*, *C. perfringens* Type C toxoid and *C. novyi* Type B toxoid.

The vaccine formulation 2 alone or in combination with SUISENG® was subsequently used in Example 3.

Example 2: Serological Response Against *C. difficile* TcdA and TcdB Toxoid of Pigs Immunized with a Vaccine of the Invention A total of 24 pigs of 12 weeks of age and free of antibodies against *C. difficile* toxins were separated into three groups of 8 pigs each one. The first group (A) received the vaccine A described in section 1.3.1 (containing a TcdA/TcdB titre of 9.4 CPE), the second group (B) received the vaccine B described in section 1.3.2. (containing a TcdA/TcdB titre of 8.4 CPE) and the third group (C) received a placebo vaccine consisting of a PBS solution. The pigs received 2 doses of 2 ml of the vaccine by the intramuscular route, administered in a 3 week interval between the first (day 0) and the second dose (day 21).

In order to determine the serological response induced in the immunized animals, sera samples were taken from the animals at different days of the study (7 days before first dose of vaccine (−7), day 20, day 44 and day 55 after the first dose of vaccine) and were analyzed by ELISA to detect the presence of antibodies against TcdA/TcdB toxins of *C. difficile*.

Figure 1:
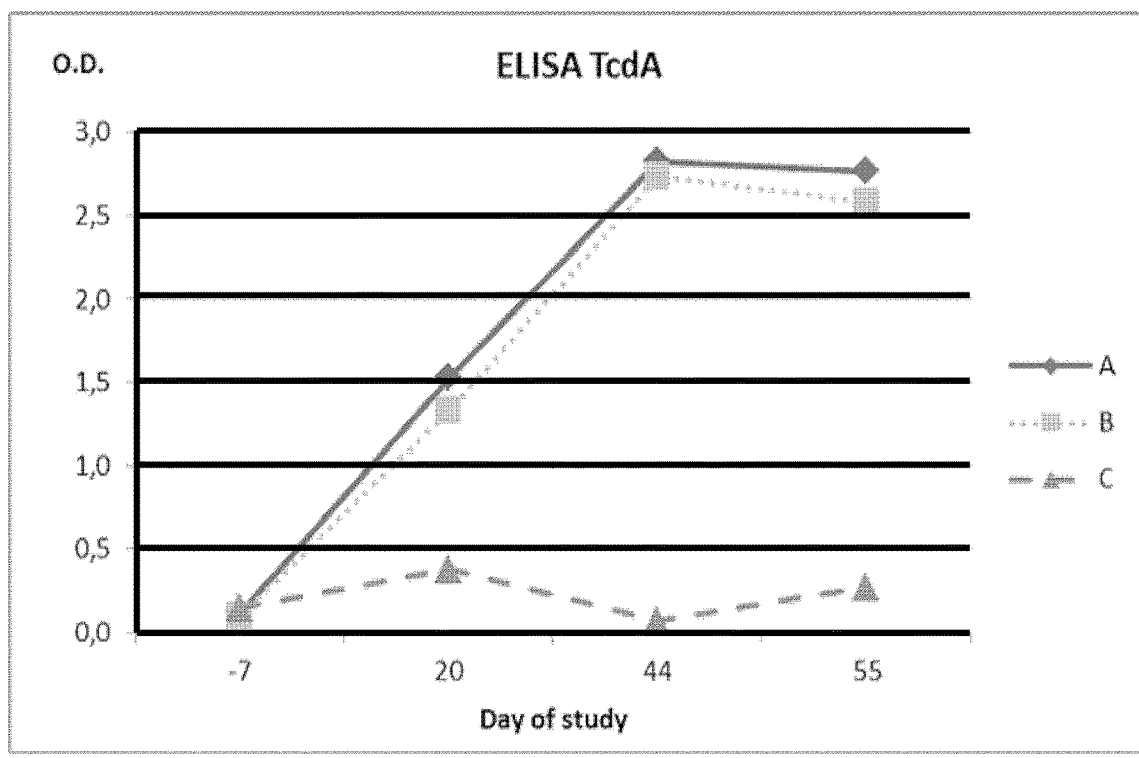
FIG. 1, related with Example 2, shows the serologic response of pigs against *C. difficile* toxoid A TdcA (A) and toxoid B TcdB (B), groups A to C. Group A corresponds to pigs vaccinated with *C. difficile* toxoids A and B (at 9.4 CPE); group B corresponds to pigs vaccinated with *C. difficile* toxoids A and B (at 8.4 CPE); and group C corresponds to pigs vaccinated with a placebo vaccine. The O.D. (ELISA optical density, mean of the group) is represented on the y-axis as an indicator of the IgG antibody response.
Figure 1:
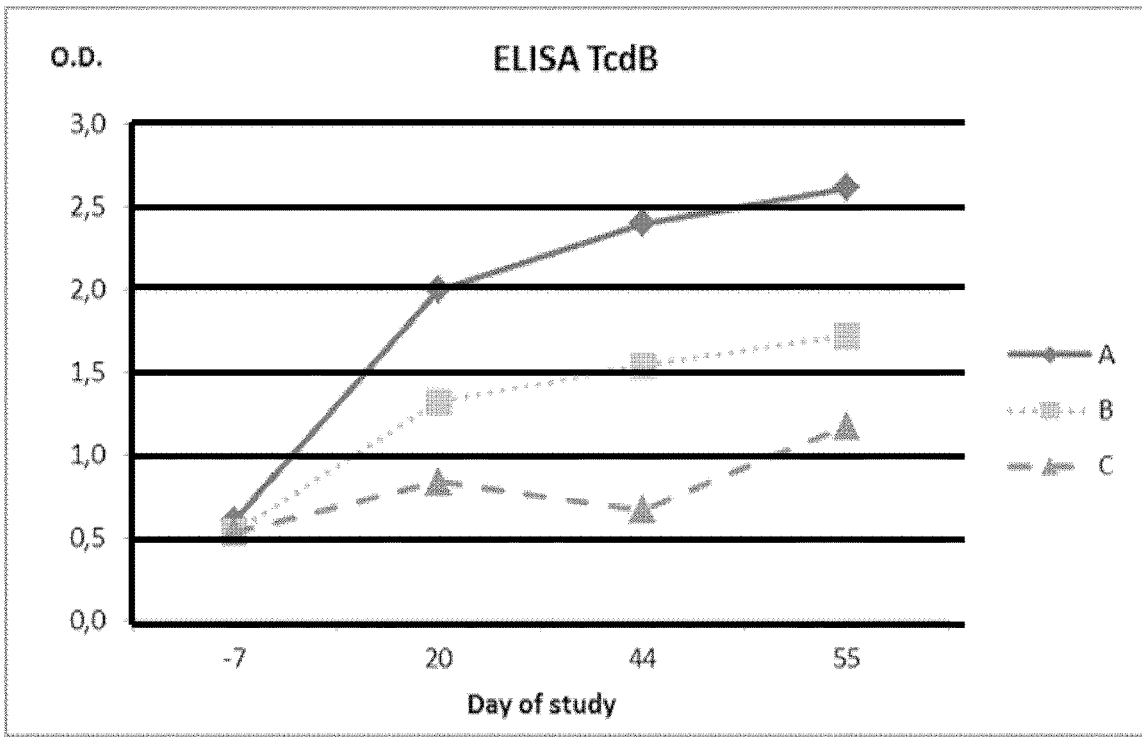

The results clearly demonstrated an increase of antibody levels for both antigens in the vaccinated groups compared to the control group (FIGS. 1, A and B). Accordingly, the vaccine of the invention showed a clear immune response against TcdA and TcdB toxins of *C. difficile*, further it was observed that the antibodies were neutralizing antibodies.

Example 3: Serological Response of Sows Immunized with Different Combination Vaccines A total of 16 pregnant sows at 6 weeks before farrowing and free of antibodies against *C. perfringens* Type A alpha toxin and *C. difficile* TcdA and TcdB toxins were selected for this study. The sows were divided into four different groups of 4 animals each one (A to D). Each group received a different treatment:

Group A: Vaccine 1 in combination with SUISENG® as described in section 1.3.3
Group B: Vaccine 2 in combination with SUISENG® as described in section 1.3.4
Group C: Vaccine 2 alone (without SUISENG®).
Group D: placebo vaccine (adjuvant without the antigenic phase).

All groups were immunized with the same administration plan. The administration plan consisted of 2 doses of 2 ml administered by intramuscular route with an interval of 3 weeks between them. The first dose was administered 6 weeks before parturition (day 0) and the second dose 3 weeks before (day 21) parturition. The first dose was given in the right side of the neck and second dose in the left side. The groups that were vaccinated also with SUISENG® (A, B groups) received a 4 ml-shot, as the SUISENG® was mixed at a ratio 1:1 with the experimental vaccine, so a 2 ml-shot for each vaccine was used in the vaccine protocol.

Serological Response of Sows Against *C. difficile* and *C. perfringens* Antigens The analysis of the serological response against the antigens present in the vaccine of the invention was developed using two techniques: ELISA and seroneutralization. Serum was extracted at the day of the first vaccination (day 0) and at days 20 and 44 after the first vaccination.

It was observed a clear seroconversion to all antigens for both *C. difficile* and *C. perfringens* in all animals that were immunized in comparison to the control group (FIG. 3).

Serological Response of Sows Immunized with a Combined Vaccine

In order to determine the serological response induced by the SUISENG®, sera of sows of all four groups were extracted at day 44 after the first vaccination and analyzed by ELISA to detect the presence of antibodies against SUISENG® antigens (FIG. 2). A clear seroconversion was also observed for the groups A and B for all antigens. These results indicate that the association of SUISENG® with the vaccine of the invention performs well and the efficacy of SUISENG® is also satisfactory when combined with the vaccine of the invention.

Antibodies in Colostrum

In order to determine the maternal immunity transfer, colostrum of all sows was collected at the day of birth. The serological response was analyzed by ELISA and seroneutralization to detect specific antibodies against *C. perfringens* Type A alpha toxin and *C. difficile* TcdA and TcdB toxins.

It was observed that the samples of colostrum collected from the immunized animals contained very high titres of specific antibodies against *C. perfringens* Type A alpha toxin and *C. difficile* TcdA and TcdB toxins when compared to the placebo group (FIG. 4).

Example 4: Efficacy of the Vaccine of the Invention by Passive Immunization to Piglets In this Example the efficacy of the vaccine was assessed after an experimental infection in piglets immunized passively via colostrum.

A total of 98 new-born piglets were used in this study. The piglets came from the sows immunized in the Example 3. The new-born piglets of each sow were sorted into three groups. Each group received a different challenge. The distribution is described in Table 2.

TABLE 2

Summary of the piglet distribution groups.

| Challenge group (Example 3) | No of sows | No of piglets | Challenge | Piglet Experimental group |
|---|---|---|---|---|
| A | 4 | 8 | *C. perfringens* | A-1 |
| | | 8 | *C. difficile* | A-2 |
| | | 7 | — | A-3 |
| B | 4 | 8 | *C. perfringens* | B-1 |
| | | 8 | C. difficile | B-2 |
| | | 8 | — | B-3 |
| C | 4 | 7 | C. perfringens | C-1 |
| | | 7 | *C. difficile* | C-2 |
| | | 7 | — | C-3 |
| D | 4 | 10 | *C. perfringens* | D-1 |
| | | 10 | *C. difficile* | D-2 |
| | | 10 | — | D-3 |

The experimental challenge was given to one-day-old piglets by intraperitoneal route with a 2 ml injection. The piglets were challenged with the $DL_{100\%}$ dose of each toxin titrated previously. The toxins were obtained by a process analogous to that described in the Example 1 but without the inactivation step (homologous challenge).

As performed in sows in Example 3, blood at the day of birth was extracted from piglets to obtain sera in order to analyze it serologically by ELISA and seroneutralization. It was observed that all animals that came from immunized sows contained high levels of specific maternal antibodies against *C. perfringens* Type A alpha toxin and *C. difficile* TcdA/TcdB toxins. This example demonstrates that the antibody transfer via colostrum occurred efficiently in all immunized groups.

In order to determine the efficacy of the vaccine in piglets, all piglets dead and surviving were necropsied (surviving piglets necropsied at the end of the study, day 5 after challenge). Mortality and macroscopic lesions score were determined in all the experimental groups.

The macroscopic lesions score was calculated by the sum of hydrothorax and ascites scores. These scores were assigned as 0, 1 or 2 based on the absence, mild or intense lesion observed, respectively.

Figure 5:
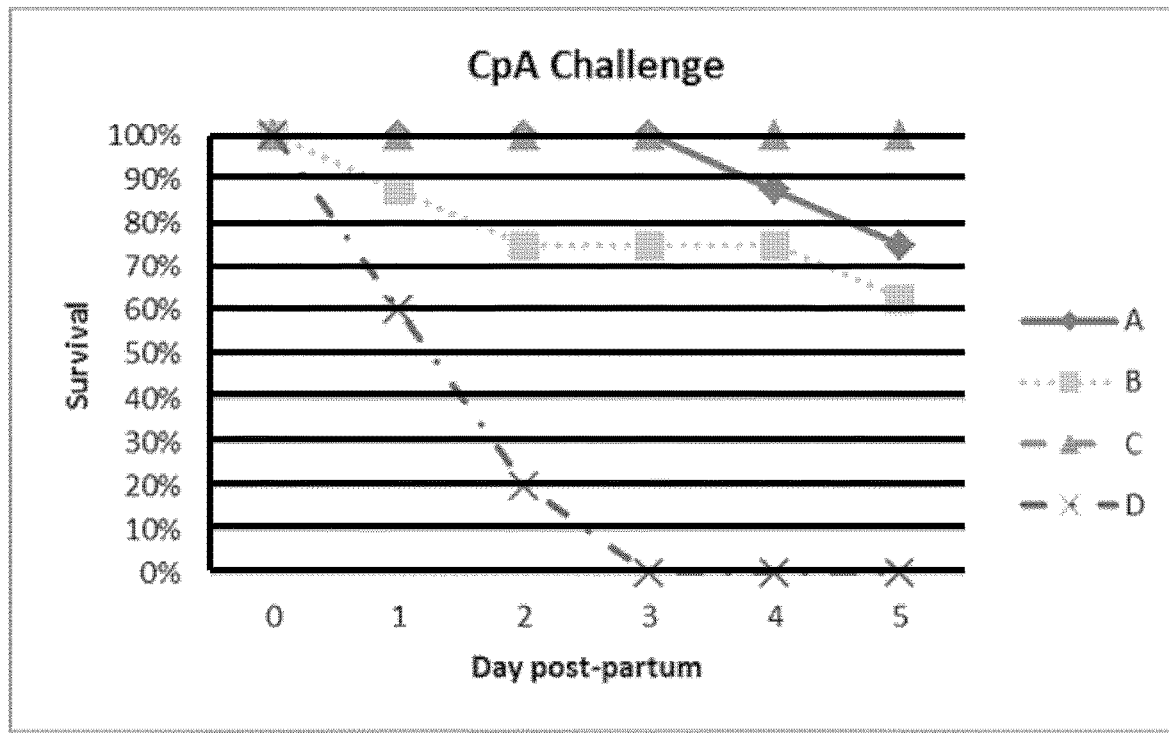
Figure 5:
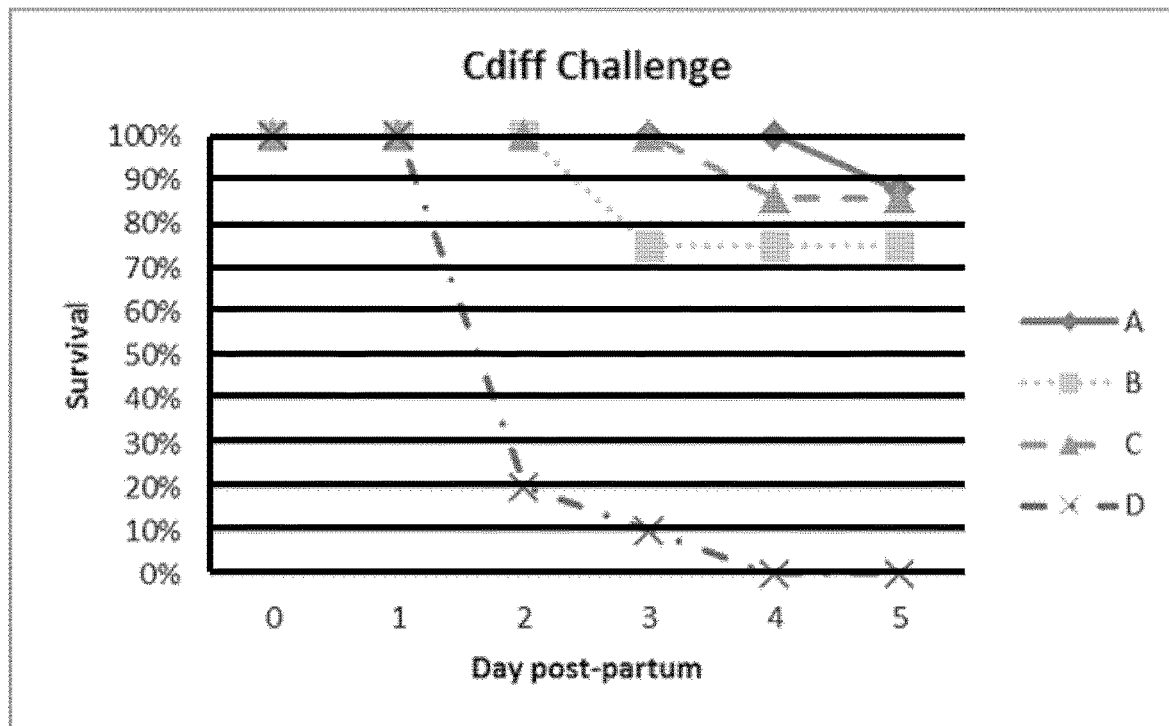

Survival assessment was the most relevant variable to assess the efficacy. Significant differences were observed between the experimental groups. A significant increase of survival was observed in piglets born from sows immunized with the vaccine of the invention (FIG. 5).

A significant reduction of macroscopic lesion score between the immunized groups (A, B, C) with respect to the placebo group (D) was also observed (FIG. 6).

Additional multivalent vaccines of the invention were also tested in swine and the animals were challenged also with heterologous *C. difficile* and *C. perfringens* Type A strains. The assays were performed with different titres of CPE for the TcdA and TcdB toxoids of *C. difficile* and different titres of HA for the alpha toxoid of *C. perfringens* Type A. The assays included CPE titres of *C. difficile* TcdA/TcdB toxoid as low as 6.7, 7.0, 7.3, 7.8 and 8.0 CPE. Similarly, HA titers of *C. perfringens* Type A alpha toxoid were as low as 11.0 and 12.0 HA. In addition, activities of 15.3, 16.3 and 17.3 were also tested for *C. perfringens* Type A alpha toxoid in combination with *C. difficile* TcdA/TcdB toxoids. These additionally vaccines were produced following the same protocols described in the above examples. The vaccines were also formulated with the same adjuvants as those described in the above examples. The vaccines tested also included the combination with SUISENG® (LABORATORIOS HIPRA, S.A.) at a 1:1 ratio as previously described.

The results obtained with all the additional formulations tested at different CPE and HA activities for *C. difficile* and *C. perfringens* Type A, respectively, showed significantly differences in the serological responses. In particular, the antibodies titers in the vaccinated pregnant sows were significantly higher than in non-vaccinated ones. In addition, significant differences regarding survival were observed between the piglets from vaccinated and non-vaccinated pregnant sows. The survival rates observed were also significantly higher in the former group.

From the results obtained with all formulations tested it can be concluded that all of them were effective. A survival rate above 50% and/or mean of lesions (sum hydrothorax and ascites scores)<1 for both challenges was a good indicator of the efficacy of the tested vaccines. Furthermore, when the experimental vaccines of the examples were associated with other antigens, such as the antigens present in SUISENG®, no significant decrease on efficacy was observed demonstrating a good compatibility between SUISENG® and the vaccine of the invention.

All the results obtained sustain that the immunologic response of the vaccines of the invention in the vaccinated pregnant sows fully correlates with the maternal passive immunity response transferred to the progeny so that a protective effect of the said vaccines are obtained in the piglets, even from the first day of life.

CITATION LIST

Patent Literature

WO2014144567A2
US20150140033A1

Non-Patent Literature

1. Arroyo, L. G. et al. PCR ribotyping of *Clostridium difficile* isolates originating from human and animal sources. *J. Med. Microbiol.* 54, 163-166 (2005).
2. Debast, S. B. et al. *Clostridium difficile* PCR ribotype 078 toxinotype V found in diarrhoeal pigs identical to isolates from affected humans. *Environ. Microbiol.* 11, 505-511 (2009).
3. Lawley, T. D. et al. Antibiotic treatment of *Clostridium difficile* carrier mice triggers a supershedder state, spore-mediated transmission, and severe disease in immunocompromised hosts. *Infect. Immun.* 77, 3661-3669 (2009).
4. Carter, G. P., Rood, J. I. & Lyras, D. The role of toxin A and toxin B in *Clostridium difficile*-associated disease. Past and present perspectives. *Nature* 1, 58-64 (2010).
5. Voth, D. E. & Ballard, J. D. *Clostridium difficile* Toxins: Mechanism of Action and Role in Disease. *Clin. Microbiol. Rev.* 18, 247-263 (2005).
6. Barroso, L. A., Wang, S.-Z., Phelps, C. J., Johnson, J. L. & Wilkins, T. D. Nucleotide sequence of *Clostridium difficile* toxin B gene. *Nucleic Acids Res.* 18, 7499 (1990).
7. Dove, C. H. et al. Molecular characterization of the *Clostridium difficile* toxin A gene. *Infect. Immun.* 58, 480-488 (1990).
8. Anderson, M. A. & Songer, J. G. Evaluation of two enzyme immunoassays for detection of *Clostridium difficile* toxins A and B in swine. *Vet. Microbiol.* 128, 204-206 (2008).
9. Songer, J. G. The emergence of *Clostridium difficile* as a pathogen of food animals. *Anim. Heal. Res. Rev.* 5, 321-326 (2004).
10. Songer, J. G. & Uzal, F. A. Clostridial Enteric Infections in Pigs. J. Vet. Diagnostic Investig. 17, 528-536 (2005).
11. Chan, G. et al. The epidemiology of *Clostridium perfringens* type a on Ontario swine farms, with special reference to cpb2-positive isolates. *BMC Vet. Res.* 8, 156 (2012).
12. Cruz-Junior, E. C. et al. A surveillance of enteropathogens in piglets from birth to seven days of age in Brazil. *Pesqui. Vet. Bras.* 33, 963-969 (2013).
13. Justin, N. et al. The first strain of *Clostridium perfringens* isolated from an avian source has an alpha-toxin with divergent structural and kinetic properties. *Biochemistry* 41, 6253-6262 (2002).

The invention claimed is:

1. A method for providing maternal passive immunity to the progeny of a livestock female against a disease caused by *Clostridium* sp. that comprises administering a vaccine to a pregnant female livestock animal prior to the birth of the progeny, thereby immunizing the livestock in need thereof with the administered vaccine, wherein the vaccine comprises an immunogenic composition comprising:

(a) one or more *C. difficile* toxoid selected from the group consisting of a *C. difficile* A toxoid (TcdA), a *C. difficile* B toxoid (TcdB), and mixtures thereof; and (b) one or more *C. perfringens* Type A alpha toxoid;

and a pharmaceutically acceptable excipient and/or carrier.

2. The method according to claim 1, wherein the method of providing maternal passive immunity comprises the administration of at least two doses to the pregnant female livestock animal.

3. The method according to claim 1 wherein the immunogenic composition or the vaccine is administered intranasally, intradermally, transmucosally (mucosally and/or submucosally), subcutaneously, by means of aerosol, intramuscularly, intravenously, or orally.

4. The method according to claim 1, wherein the immunogenic composition comprises a *C. difficile* A toxoid, a *C. difficile* B toxoid, and a *C. perfringens* Type A *alpha* toxoid.

5. The method according to claim 1, wherein the immunogenic composition further comprises one or more additional antigens, wherein the additional antigen is selected from a group of microorganisms consisting of *Actinobacillus, Bordetella, Borrelia, Brachyspira, Brucella, Campylobacter, Chlamydia* and *Chlamydophila, Clostridium, Corynebacterium, Enterococcus, Erysipelothrix, Escherichia, Francisella, Haemophilus, Helicobacter, Isospora, Lawsonia, Legionella, Leptospira, Listeria, Mycobacterium, Mycoplasma, Neisseria, Pasteurella, Pseudomonas, Rickettsia, Salmonella, Shigella, Staphylococcus, Streptococcus, Treponema Vibrio* and *Yersinia* genus, porcine reproductive and respiratory syndrome virus, swine influenza virus, contagious gastroenteritis virus, porcine parvovirus, encephalomyocarditis virus, coronavirus, rotavirus, porcine periweaning failure to thrive syndrome agent, classical swine fever virus, African swine fever virus, calicivirus, torque teno virus (TTV), transmissible gastroenteritis coronavirus (TGEV), porcine epidemic diarrhea virus (PED), porcine circovirus and combinations thereof.

6. The method according to claim 5, wherein the one or more additional antigens are selected from the group consisting of *E. coli* F4ab, F4ac, F5 and F6 fimbrial adhesins, *E. coli* LT enterotoxoid, *C. perfringens* Type C toxoid, *C. novyi* Type B toxoid, and combinations thereof.

7. The method according to claim 1, wherein the vaccine further comprises an adjuvant.

* * * * *

SEQUENCE LISTING

```
<160> NUMBER OF SEQ ID NOS: 3

<210> SEQ ID NO 1
<211> LENGTH: 2710
<212> TYPE: PRT
<213> ORGANISM: Clostridium difficile
<220> FEATURE:
<221> NAME/KEY: mat_peptide
<222> LOCATION: (1)..(2710)
<223> OTHER INFORMATION: Toxin A
```

```
<400> SEQUENCE: 1

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Glu Asn Lys Tyr Leu Gln Leu
        35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
        210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
```

```
                    405                 410                 415
Ile Glu Ser Asp Asn Asn Phe Thr Asp Thr Thr Lys Ile Phe His Asp
                420                 425                 430

Ser Leu Phe Asn Ser Ala Thr Ala Glu Asn Ser Met Phe Leu Thr Lys
                435                 440                 445

Ile Ala Pro Tyr Leu Gln Val Gly Phe Met Pro Glu Ala Arg Ser Thr
            450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
                500                 505                 510

Gln Glu Ile Asn Ser Leu Trp Ser Phe Asp Gln Ala Ser Ala Lys Tyr
                515                 520                 525

Gln Phe Glu Lys Tyr Val Arg Asp Tyr Thr Gly Gly Ser Leu Ser Glu
                530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Glu Ala Gly Ser
                565                 570                 575

Lys Asn Tyr Val His Tyr Ile Ile Gln Leu Gln Gly Asp Asp Ile Ser
                580                 585                 590

Tyr Glu Ala Thr Cys Asn Leu Phe Ser Lys Asn Pro Lys Asn Ser Ile
                595                 600                 605

Ile Ile Gln Arg Asn Met Asn Glu Ser Ala Lys Ser Tyr Phe Leu Ser
            610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
            675                 680                 685

Ser Pro Lys Asn Val Glu Val Asn Leu Leu Gly Cys Asn Met Phe Ser
            690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
            755                 760                 765

Ala Ile Met Ser Asp Leu Ser Ser Lys Glu Tyr Ile Phe Phe Asp Ser
            770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
                820                 825                 830
```

```
Ser Ile Gly Asp Tyr Ile Tyr Tyr Glu Lys Leu Glu Pro Val Lys Asn
        835                 840                 845
Ile Ile His Asn Ser Ile Asp Asp Leu Ile Asp Glu Phe Asn Leu Leu
850                 855                 860
Glu Asn Val Ser Asp Glu Leu Tyr Glu Leu Lys Lys Leu Asn Asn Leu
865                 870                 875                 880
Asp Glu Lys Tyr Leu Ile Ser Phe Glu Asp Ile Ser Lys Asn Asn Ser
            885                 890                 895
Thr Tyr Ser Val Arg Phe Ile Asn Lys Ser Asn Gly Glu Ser Val Tyr
                900                 905                 910
Val Glu Thr Glu Lys Glu Ile Phe Ser Lys Tyr Ser His Ile Thr
            915                 920                 925
Lys Glu Ile Ser Thr Ile Lys Asn Ser Ile Ile Thr Asp Val Asn Gly
            930                 935                 940
Asn Leu Leu Asp Asn Ile Gln Leu Asp His Thr Ser Gln Val Asn Thr
945                 950                 955                 960
Leu Asn Ala Ala Phe Phe Ile Gln Ser Leu Ile Asp Tyr Ser Ser Asn
                965                 970                 975
Lys Asp Val Leu Asn Asp Leu Ser Thr Ser Val Lys Val Gln Leu Tyr
            980                 985                 990
Ala Gln Leu Phe Ser Thr Gly Leu Asn Thr Ile Tyr Asp Ser Ile Gln
            995                 1000                1005
Leu Val Asn Leu Ile Ser Asn Ala Val Asn Asp Thr Ile Asn Val
    1010                1015                1020
Leu Pro Thr Ile Thr Glu Gly Ile Pro Ile Val Ser Thr Ile Leu
    1025                1030                1035
Asp Gly Ile Asn Leu Gly Ala Ala Ile Lys Glu Leu Leu Asp Glu
    1040                1045                1050
His Asp Pro Leu Leu Lys Lys Glu Leu Glu Ala Lys Val Gly Val
    1055                1060                1065
Leu Ala Ile Asn Met Ser Leu Ser Ile Ala Ala Thr Val Ala Ser
    1070                1075                1080
Ile Val Gly Ile Gly Ala Glu Val Thr Ile Phe Leu Leu Pro Ile
    1085                1090                1095
Ala Gly Ile Ser Ala Gly Ile Pro Ser Leu Val Asn Asn Glu Leu
    1100                1105                1110
Ile Leu His Asp Lys Ala Thr Ser Val Val Asn Tyr Phe Asn His
    1115                1120                1125
Leu Ser Glu Ser Lys Lys Tyr Gly Pro Leu Lys Thr Glu Asp Asp
    1130                1135                1140
Lys Ile Leu Val Pro Ile Asp Asp Leu Val Ile Ser Glu Ile Asp
    1145                1150                1155
Phe Asn Asn Asn Ser Ile Lys Leu Gly Thr Cys Asn Ile Leu Ala
    1160                1165                1170
Met Glu Gly Gly Ser Gly His Thr Val Thr Gly Asn Ile Asp His
    1175                1180                1185
Phe Phe Ser Ser Pro Ser Ile Ser Ser His Ile Pro Ser Leu Ser
    1190                1195                1200
Ile Tyr Ser Ala Ile Gly Ile Glu Thr Glu Asn Leu Asp Phe Ser
    1205                1210                1215
Lys Lys Ile Met Met Leu Pro Asn Ala Pro Ser Arg Val Phe Trp
    1220                1225                1230
```

-continued

| | | | | | | | | | | |
|---|---|---|---|---|---|---|---|---|---|---|
| Trp | Glu 1235 | Thr | Gly | Ala | Val 1240 | Pro | Gly | Leu | Arg 1245 | Ser | Leu | Glu | Asn | Asp |
| Gly | Thr 1250 | Arg | Leu | Leu | Asp 1255 | Ser | Ile | Arg | Asp 1260 | Leu | Tyr | Pro | Gly | Lys |
| Phe | Tyr 1265 | Trp | Arg | Phe | Tyr 1270 | Ala | Phe | Phe | Asp 1275 | Tyr | Ala | Ile | Thr | Thr |
| Leu | Lys 1280 | Pro | Val | Tyr | Glu 1285 | Asp | Thr | Asn | Ile 1290 | Lys | Ile | Lys | Leu | Asp |
| Lys | Asp 1295 | Thr | Arg | Asn | Phe 1300 | Ile | Met | Pro | Thr 1305 | Ile | Thr | Thr | Asn | Glu |
| Ile | Arg 1310 | Asn | Lys | Leu | Ser 1315 | Tyr | Ser | Phe | Asp 1320 | Gly | Ala | Gly | Gly | Thr |
| Tyr | Ser 1325 | Leu | Leu | Leu | Ser 1330 | Ser | Tyr | Pro | Ile 1335 | Ser | Thr | Asn | Ile | Asn |
| Leu | Ser 1340 | Lys | Asp | Asp | Leu 1345 | Trp | Ile | Phe | Asn 1350 | Ile | Asp | Asn | Glu | Val |
| Arg | Glu 1355 | Ile | Ser | Ile | Glu 1360 | Asn | Gly | Thr | Ile 1365 | Lys | Lys | Gly | Lys | Leu |
| Ile | Lys 1370 | Asp | Val | Leu | Ser 1375 | Lys | Ile | Asp | Ile 1380 | Asn | Lys | Asn | Lys | Leu |
| Ile | Ile 1385 | Gly | Asn | Gln | Thr 1390 | Ile | Asp | Phe | Ser 1395 | Gly | Asp | Ile | Asp | Asn |
| Lys | Asp 1400 | Arg | Tyr | Ile | Phe 1405 | Leu | Thr | Cys | Glu 1410 | Leu | Asp | Asp | Lys | Ile |
| Ser | Leu 1415 | Ile | Ile | Glu | Ile 1420 | Asn | Leu | Val | Ala 1425 | Lys | Ser | Tyr | Ser | Leu |
| Leu | Leu 1430 | Ser | Gly | Asp | Lys 1435 | Asn | Tyr | Leu | Ile 1440 | Ser | Asn | Leu | Ser | Asn |
| Thr | Ile 1445 | Glu | Lys | Ile | Asn 1450 | Thr | Leu | Gly | Leu 1455 | Asp | Ser | Lys | Asn | Ile |
| Ala | Tyr 1460 | Asn | Tyr | Thr | Asp 1465 | Glu | Ser | Asn | Asn 1470 | Lys | Tyr | Phe | Gly | Ala |
| Ile | Ser 1475 | Lys | Thr | Ser | Gln 1480 | Lys | Ser | Ile | Ile 1485 | His | Tyr | Lys | Lys | Asp |
| Ser | Lys 1490 | Asn | Ile | Leu | Glu 1495 | Phe | Tyr | Asn | Asp 1500 | Ser | Thr | Leu | Glu | Phe |
| Asn | Ser 1505 | Lys | Asp | Phe | Ile 1510 | Ala | Glu | Asp | Ile 1515 | Asn | Val | Phe | Met | Lys |
| Asp | Asp 1520 | Ile | Asn | Thr | Ile 1525 | Thr | Gly | Lys | Tyr 1530 | Tyr | Val | Asp | Asn | Asn |
| Thr | Asp 1535 | Lys | Ser | Ile | Asp 1540 | Phe | Ser | Ile | Ser 1545 | Leu | Val | Ser | Lys | Asn |
| Gln | Val 1550 | Lys | Val | Asn | Gly 1555 | Leu | Tyr | Leu | Asn 1560 | Glu | Ser | Val | Tyr | Ser |
| Ser | Tyr 1565 | Leu | Asp | Phe | Val 1570 | Lys | Asn | Ser | Asp 1575 | Gly | His | His | Asn | Thr |
| Ser | Asn 1580 | Phe | Met | Asn | Leu 1585 | Phe | Leu | Asp | Asn 1590 | Ile | Ser | Phe | Trp | Lys |
| Leu | Phe 1595 | Gly | Phe | Glu | Asn 1600 | Ile | Asn | Phe | Val 1605 | Ile | Asp | Lys | Tyr | Phe |
| Thr | Leu 1610 | Val | Gly | Lys | Thr 1615 | Asn | Leu | Gly | Tyr 1620 | Val | Glu | Phe | Ile | Cys |
| Asp | Asn | Asn | Lys | Asn | Ile | Asp | Ile | Tyr | Phe | Gly | Glu | Trp | Lys | Thr |

-continued

```
             1625                1630                1635
Ser  Ser  Ser  Lys  Ser  Thr  Ile  Phe  Ser  Gly  Asn  Gly  Arg  Asn  Val
             1640                1645                1650

Val  Val  Glu  Pro  Ile  Tyr  Asn  Pro  Asp  Thr  Gly  Glu  Asp  Ile  Ser
             1655                1660                1665

Thr  Ser  Leu  Asp  Phe  Ser  Tyr  Glu  Pro  Leu  Tyr  Gly  Ile  Asp  Arg
             1670                1675                1680

Tyr  Ile  Asn  Lys  Val  Leu  Ile  Ala  Pro  Asp  Leu  Tyr  Thr  Ser  Leu
             1685                1690                1695

Ile  Asn  Ile  Asn  Thr  Asn  Tyr  Tyr  Ser  Asn  Glu  Tyr  Tyr  Pro  Glu
             1700                1705                1710

Ile  Ile  Val  Leu  Asn  Pro  Asn  Thr  Phe  His  Lys  Lys  Val  Asn  Ile
             1715                1720                1725

Asn  Leu  Asp  Ser  Ser  Ser  Phe  Glu  Tyr  Lys  Trp  Ser  Thr  Glu  Gly
             1730                1735                1740

Ser  Asp  Phe  Ile  Leu  Val  Arg  Tyr  Leu  Glu  Glu  Ser  Asn  Lys  Lys
             1745                1750                1755

Ile  Leu  Gln  Lys  Ile  Arg  Ile  Lys  Gly  Ile  Leu  Ser  Asn  Thr  Gln
             1760                1765                1770

Ser  Phe  Asn  Lys  Met  Ser  Ile  Asp  Phe  Lys  Asp  Ile  Lys  Lys  Leu
             1775                1780                1785

Ser  Leu  Gly  Tyr  Ile  Met  Ser  Asn  Phe  Lys  Ser  Phe  Asn  Ser  Glu
             1790                1795                1800

Asn  Glu  Leu  Asp  Arg  Asp  His  Leu  Gly  Phe  Lys  Ile  Ile  Asp  Asn
             1805                1810                1815

Lys  Thr  Tyr  Tyr  Tyr  Asp  Glu  Asp  Ser  Lys  Leu  Val  Lys  Gly  Leu
             1820                1825                1830

Ile  Asn  Ile  Asn  Asn  Ser  Leu  Phe  Tyr  Phe  Asp  Pro  Ile  Glu  Phe
             1835                1840                1845

Asn  Leu  Val  Thr  Gly  Trp  Gln  Thr  Ile  Asn  Gly  Lys  Lys  Tyr  Tyr
             1850                1855                1860

Phe  Asp  Ile  Asn  Thr  Gly  Ala  Ala  Leu  Thr  Ser  Tyr  Lys  Ile  Ile
             1865                1870                1875

Asn  Gly  Lys  His  Phe  Tyr  Phe  Asn  Asn  Asp  Gly  Val  Met  Gln  Leu
             1880                1885                1890

Gly  Val  Phe  Lys  Gly  Pro  Asp  Gly  Phe  Glu  Tyr  Phe  Ala  Pro  Ala
             1895                1900                1905

Asn  Thr  Gln  Asn  Asn  Asn  Ile  Glu  Gly  Gln  Ala  Ile  Val  Tyr  Gln
             1910                1915                1920

Ser  Lys  Phe  Leu  Thr  Leu  Asn  Gly  Lys  Lys  Tyr  Tyr  Phe  Asp  Asn
             1925                1930                1935

Asn  Ser  Lys  Ala  Val  Thr  Gly  Trp  Arg  Ile  Ile  Asn  Asn  Glu  Lys
             1940                1945                1950

Tyr  Tyr  Phe  Asn  Pro  Asn  Asn  Ala  Ile  Ala  Ala  Val  Gly  Leu  Gln
             1955                1960                1965

Val  Ile  Asp  Asn  Asn  Lys  Tyr  Tyr  Phe  Asn  Pro  Asp  Thr  Ala  Ile
             1970                1975                1980

Ile  Ser  Lys  Gly  Trp  Gln  Thr  Val  Asn  Gly  Ser  Arg  Tyr  Tyr  Phe
             1985                1990                1995

Asp  Thr  Asp  Thr  Ala  Ile  Ala  Phe  Asn  Gly  Tyr  Lys  Thr  Ile  Asp
             2000                2005                2010

Gly  Lys  His  Phe  Tyr  Phe  Asp  Ser  Asp  Cys  Val  Val  Lys  Ile  Gly
             2015                2020                2025
```

```
Val Phe Ser Thr Ser Asn Gly Phe Glu Tyr Phe Ala Pro Ala Asn
    2030            2035            2040

Thr Tyr Asn Asn Asn Ile Glu Gly Gln Ala Ile Val Tyr Gln Ser
    2045            2050            2055

Lys Phe Leu Thr Leu Asn Gly Lys Lys Tyr Tyr Phe Asp Asn Asn
    2060            2065            2070

Ser Lys Ala Val Thr Gly Leu Gln Thr Ile Asp Ser Lys Lys Tyr
    2075            2080            2085

Tyr Phe Asn Thr Asn Thr Ala Glu Ala Ala Thr Gly Trp Gln Thr
    2090            2095            2100

Ile Asp Gly Lys Lys Tyr Tyr Phe Asn Thr Asn Thr Ala Glu Ala
    2105            2110            2115

Ala Thr Gly Trp Gln Thr Ile Asp Gly Lys Lys Tyr Tyr Phe Asn
    2120            2125            2130

Thr Asn Thr Ala Ile Ala Ser Thr Gly Tyr Thr Ile Ile Asn Gly
    2135            2140            2145

Lys His Phe Tyr Phe Asn Thr Asp Gly Ile Met Gln Ile Gly Val
    2150            2155            2160

Phe Lys Gly Pro Asn Gly Phe Glu Tyr Phe Ala Pro Ala Asn Thr
    2165            2170            2175

Asp Ala Asn Asn Ile Glu Gly Gln Ala Ile Leu Tyr Gln Asn Glu
    2180            2185            2190

Phe Leu Thr Leu Asn Gly Lys Lys Tyr Tyr Phe Gly Ser Asp Ser
    2195            2200            2205

Lys Ala Val Thr Gly Trp Arg Ile Ile Asn Asn Lys Lys Tyr Tyr
    2210            2215            2220

Phe Asn Pro Asn Asn Ala Ile Ala Ala Ile His Leu Cys Thr Ile
    2225            2230            2235

Asn Asn Asp Lys Tyr Tyr Phe Ser Tyr Asp Gly Ile Leu Gln Asn
    2240            2245            2250

Gly Tyr Ile Thr Ile Glu Arg Asn Asn Phe Tyr Phe Asp Ala Asn
    2255            2260            2265

Asn Glu Ser Lys Met Val Thr Gly Val Phe Lys Gly Pro Asn Gly
    2270            2275            2280

Phe Glu Tyr Phe Ala Pro Ala Asn Thr His Asn Asn Asn Ile Glu
    2285            2290            2295

Gly Gln Ala Ile Val Tyr Gln Asn Lys Phe Leu Thr Leu Asn Gly
    2300            2305            2310

Lys Lys Tyr Tyr Phe Asp Asn Asp Ser Lys Ala Val Thr Gly Trp
    2315            2320            2325

Gln Thr Ile Asp Gly Lys Lys Tyr Tyr Phe Asn Leu Asn Thr Ala
    2330            2335            2340

Glu Ala Ala Thr Gly Trp Gln Thr Ile Asp Gly Lys Lys Tyr Tyr
    2345            2350            2355

Phe Asn Leu Asn Thr Ala Glu Ala Ala Thr Gly Trp Gln Thr Ile
    2360            2365            2370

Asp Gly Lys Lys Tyr Tyr Phe Asn Thr Asn Thr Phe Ile Ala Ser
    2375            2380            2385

Thr Gly Tyr Thr Ser Ile Asn Gly Lys His Phe Tyr Phe Asn Thr
    2390            2395            2400

Asp Gly Ile Met Gln Ile Gly Val Phe Lys Gly Pro Asn Gly Phe
    2405            2410            2415
```

```
Glu Tyr Phe Ala Pro Ala Asn Thr Asp Ala Asn Asn Ile Glu Gly
            2420            2425                2430

Gln Ala Ile Leu Tyr Gln Asn Lys Phe Leu Thr Leu Asn Gly Lys
2435                2440                2445

Lys Tyr Tyr Phe Gly Ser Asp Ser Lys Ala Val Thr Gly Leu Arg
    2450                2455                2460

Thr Ile Asp Gly Lys Lys Tyr Tyr Phe Asn Thr Asn Thr Ala Val
2465                2470                2475

Ala Val Thr Gly Trp Gln Thr Ile Asn Gly Lys Lys Tyr Tyr Phe
    2480                2485                2490

Asn Thr Asn Thr Ser Ile Ala Ser Thr Gly Tyr Thr Ile Ile Ser
    2495                2500                2505

Gly Lys His Phe Tyr Phe Asn Thr Asp Gly Ile Met Gln Ile Gly
2510                2515                2520

Val Phe Lys Gly Pro Asp Gly Phe Glu Tyr Phe Ala Pro Ala Asn
    2525                2530                2535

Thr Asp Ala Asn Asn Ile Glu Gly Gln Ala Ile Arg Tyr Gln Asn
2540                2545                2550

Arg Phe Leu Tyr Leu His Asp Asn Ile Tyr Tyr Phe Gly Asn Asn
    2555                2560                2565

Ser Lys Ala Ala Thr Gly Trp Val Thr Ile Asp Gly Asn Arg Tyr
    2570                2575                2580

Tyr Phe Glu Pro Asn Thr Ala Met Gly Ala Asn Gly Tyr Lys Thr
    2585                2590                2595

Ile Asp Asn Lys Asn Phe Tyr Phe Arg Asn Gly Leu Pro Gln Ile
    2600                2605                2610

Gly Val Phe Lys Gly Ser Asn Gly Phe Glu Tyr Phe Ala Pro Ala
    2615                2620                2625

Asn Thr Asp Ala Asn Asn Ile Glu Gly Gln Ala Ile Arg Tyr Gln
    2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Gly Lys Val
    2660                2665                2670

Tyr Tyr Phe Met Pro Asp Thr Ala Met Ala Ala Ala Gly Gly Leu
    2675                2680                2685

Phe Glu Ile Asp Gly Val Ile Tyr Phe Phe Gly Val Asp Gly Val
2690                2695                2700

Lys Ala Pro Gly Ile Tyr Gly
    2705                2710

<210> SEQ ID NO 2
<211> LENGTH: 2366
<212> TYPE: PRT
<213> ORGANISM: Clostridium difficile
<220> FEATURE:
<221> NAME/KEY: mat_peptide
<222> LOCATION: (1)..(2366)
<223> OTHER INFORMATION: Toxin B

<400> SEQUENCE: 2

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
```

```
                35                  40                  45
Leu Lys Asp Ile Asn Ser Leu Thr Asp Ile Tyr Ile Asp Thr Tyr Lys
 50                  55                  60
Lys Ser Gly Arg Asn Lys Ala Leu Lys Lys Phe Lys Glu Tyr Leu Val
 65                  70                  75                  80
Thr Glu Val Leu Glu Leu Lys Asn Asn Asn Leu Thr Pro Val Glu Lys
                 85                  90                  95
Asn Leu His Phe Val Trp Ile Gly Gly Gln Ile Asn Asp Thr Ala Ile
                100                 105                 110
Asn Tyr Ile Asn Gln Trp Lys Asp Val Asn Ser Asp Tyr Asn Val Asn
                115                 120                 125
Val Phe Tyr Asp Ser Asn Ala Phe Leu Ile Asn Thr Leu Lys Lys Thr
 130                 135                 140
Val Val Glu Ser Ala Ile Asn Asp Thr Leu Glu Ser Phe Arg Glu Asn
 145                 150                 155                 160
Leu Asn Asp Pro Arg Phe Asp Tyr Asn Lys Phe Phe Arg Lys Arg Met
                165                 170                 175
Glu Ile Ile Tyr Asp Lys Gln Lys Asn Phe Ile Asn Tyr Tyr Lys Ala
                180                 185                 190
Gln Arg Glu Glu Asn Pro Glu Leu Ile Ile Asp Asp Ile Val Lys Thr
                195                 200                 205
Tyr Leu Ser Asn Glu Tyr Ser Lys Glu Ile Asp Glu Leu Asn Thr Tyr
 210                 215                 220
Ile Glu Glu Ser Leu Asn Lys Ile Thr Gln Asn Ser Gly Asn Asp Val
 225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
                260                 265                 270
Arg Ile Ser Ala Leu Lys Glu Ile Gly Gly Met Tyr Leu Asp Val Asp
                275                 280                 285
Met Leu Pro Gly Ile Gln Pro Asp Leu Phe Glu Ser Ile Glu Lys Pro
 290                 295                 300
Ser Ser Val Thr Val Asp Phe Trp Glu Met Thr Lys Leu Glu Ala Ile
 305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
                340                 345                 350
Lys Ser Asp Lys Ser Glu Ile Phe Ser Ser Leu Gly Asp Met Glu Ala
                355                 360                 365
Ser Pro Leu Glu Val Lys Ile Ala Phe Asn Ser Lys Gly Ile Ile Asn
 370                 375                 380
Gln Gly Leu Ile Ser Val Lys Asp Ser Tyr Cys Ser Asn Leu Ile Val
 385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
                420                 425                 430
Asp Ser Ile Met Ala Glu Ala Asn Ala Asp Asn Gly Arg Phe Met Met
                435                 440                 445
Glu Leu Gly Lys Tyr Leu Arg Val Gly Phe Phe Pro Asp Val Lys Thr
 450                 455                 460
```

```
Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
            645                 650                 655

Glu Phe Asn Thr Asp Ile Phe Ala Gly Phe Asp Val Asp Ser Leu Ser
        660                 665                 670

Thr Glu Ile Glu Ala Ala Ile Asp Leu Ala Lys Glu Asp Ile Ser Pro
    675                 680                 685

Lys Ser Ile Glu Ile Asn Leu Leu Gly Cys Asn Met Phe Ser Tyr Ser
            690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
            725                 730                 735

Val Ser Ala Asn Gln Tyr Glu Val Arg Ile Asn Ser Glu Gly Arg Arg
        740                 745                 750

Glu Leu Leu Asp His Ser Gly Glu Trp Ile Asn Lys Glu Ser Ile
    755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
            805                 810                 815

Glu Lys Val Met Leu Thr Glu Cys Glu Ile Asn Val Ile Ser Asn Ile
        820                 825                 830

Asp Thr Gln Ile Val Glu Glu Arg Ile Glu Glu Ala Lys Asn Leu Thr
    835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880
```

```
Ser His Phe Ile Ser Phe Glu Asp Ile Ser Glu Thr Asp Glu Gly Phe
                885                 890                 895
Ser Ile Arg Phe Ile Asn Lys Glu Thr Gly Glu Ser Ile Phe Val Glu
            900                 905                 910
Thr Glu Lys Thr Ile Phe Ser Glu Tyr Ala Asn His Ile Thr Glu Glu
        915                 920                 925
Ile Ser Lys Ile Lys Gly Thr Ile Phe Asp Thr Val Asn Gly Lys Leu
    930                 935                 940
Val Lys Lys Val Asn Leu Asp Thr Thr His Glu Val Asn Thr Leu Asn
945                 950                 955                 960
Ala Ala Phe Phe Ile Gln Ser Leu Ile Glu Tyr Asn Ser Ser Lys Glu
                965                 970                 975
Ser Leu Ser Asn Leu Ser Val Ala Met Lys Val Gln Val Tyr Ala Gln
            980                 985                 990
Leu Phe Ser Thr Gly Leu Asn Thr Ile Thr Asp Ala Ala Lys Val Val
        995                 1000                1005
Glu Leu Val Ser Thr Ala Leu Asp Glu Thr Ile Asp Leu Leu Pro
    1010                1015                1020
Thr Leu Ser Glu Gly Leu Pro Ile Ile Ala Thr Ile Ile Asp Gly
    1025                1030                1035
Val Ser Leu Gly Ala Ala Ile Lys Glu Leu Ser Glu Thr Ser Asp
    1040                1045                1050
Pro Leu Leu Arg Gln Glu Ile Glu Ala Lys Ile Gly Ile Met Ala
    1055                1060                1065
Val Asn Leu Thr Thr Ala Thr Thr Ala Ile Ile Thr Ser Ser Leu
    1070                1075                1080
Gly Ile Ala Ser Gly Phe Ser Ile Leu Leu Val Pro Leu Ala Gly
    1085                1090                1095
Ile Ser Ala Gly Ile Pro Ser Leu Val Asn Asn Glu Leu Val Leu
    1100                1105                1110
Arg Asp Lys Ala Thr Lys Val Val Asp Tyr Phe Lys His Val Ser
    1115                1120                1125
Leu Val Glu Thr Glu Gly Val Phe Thr Leu Leu Asp Asp Lys Ile
    1130                1135                1140
Met Met Pro Gln Asp Asp Leu Val Ile Ser Glu Ile Asp Phe Asn
    1145                1150                1155
Asn Asn Ser Ile Val Leu Gly Lys Cys Glu Ile Trp Arg Met Glu
    1160                1165                1170
Gly Gly Ser Gly His Thr Val Thr Asp Asp Ile Asp His Phe Phe
    1175                1180                1185
Ser Ala Pro Ser Ile Thr Tyr Arg Glu Pro His Leu Ser Ile Tyr
    1190                1195                1200
Asp Val Leu Glu Val Gln Lys Glu Glu Leu Asp Leu Ser Lys Asp
    1205                1210                1215
Leu Met Val Leu Pro Asn Ala Pro Asn Arg Val Phe Ala Trp Glu
    1220                1225                1230
Thr Gly Trp Thr Pro Gly Leu Arg Ser Leu Glu Asn Asp Gly Thr
    1235                1240                1245
Lys Leu Leu Asp Arg Ile Arg Asp Asn Tyr Glu Gly Glu Phe Tyr
    1250                1255                1260
Trp Arg Tyr Phe Ala Phe Ile Ala Asp Ala Leu Ile Thr Thr Leu
    1265                1270                1275
Lys Pro Arg Tyr Glu Asp Thr Asn Ile Arg Ile Asn Leu Asp Ser
```

-continued

```
                1280                1285                1290
Asn Thr Arg Ser Phe Ile Val Pro Ile Ile Thr Thr Glu Tyr Ile
    1295                1300                1305
Arg Glu Lys Leu Ser Tyr Ser Phe Tyr Gly Ser Gly Gly Thr Tyr
    1310                1315                1320
Ala Leu Ser Leu Ser Gln Tyr Asn Met Gly Ile Asn Ile Glu Leu
    1325                1330                1335
Ser Glu Ser Asp Val Trp Ile Ile Asp Val Asp Asn Val Val Arg
    1340                1345                1350
Asp Val Thr Ile Glu Ser Asp Lys Ile Lys Lys Gly Asp Leu Ile
    1355                1360                1365
Glu Gly Ile Leu Ser Thr Leu Ser Ile Glu Glu Asn Lys Ile Ile
    1370                1375                1380
Leu Asn Ser His Glu Ile Asn Phe Ser Gly Glu Val Asn Gly Ser
    1385                1390                1395
Asn Gly Phe Val Ser Leu Thr Phe Ser Ile Leu Glu Gly Ile Asn
    1400                1405                1410
Ala Ile Ile Glu Val Asp Leu Leu Ser Lys Ser Tyr Lys Leu Leu
    1415                1420                1425
Ile Ser Gly Glu Leu Lys Ile Leu Met Leu Asn Ser Asn His Ile
    1430                1435                1440
Gln Gln Lys Ile Asp Tyr Ile Gly Phe Asn Ser Glu Leu Gln Lys
    1445                1450                1455
Asn Ile Pro Tyr Ser Phe Val Asp Ser Glu Gly Lys Glu Asn Gly
    1460                1465                1470
Phe Ile Asn Gly Ser Thr Lys Glu Gly Leu Phe Val Ser Glu Leu
    1475                1480                1485
Pro Asp Val Val Leu Ile Ser Lys Val Tyr Met Asp Asp Ser Lys
    1490                1495                1500
Pro Ser Phe Gly Tyr Tyr Ser Asn Asn Leu Lys Asp Val Lys Val
    1505                1510                1515
Ile Thr Lys Asp Asn Val Asn Ile Leu Thr Gly Tyr Tyr Leu Lys
    1520                1525                1530
Asp Asp Ile Lys Ile Ser Leu Ser Leu Thr Leu Gln Asp Glu Lys
    1535                1540                1545
Thr Ile Lys Leu Asn Ser Val His Leu Asp Glu Ser Gly Val Ala
    1550                1555                1560
Glu Ile Leu Lys Phe Met Asn Arg Lys Gly Asn Thr Asn Thr Ser
    1565                1570                1575
Asp Ser Leu Met Ser Phe Leu Glu Ser Met Asn Ile Lys Ser Ile
    1580                1585                1590
Phe Val Asn Phe Leu Gln Ser Asn Ile Lys Phe Ile Leu Asp Ala
    1595                1600                1605
Asn Phe Ile Ile Ser Gly Thr Thr Ser Ile Gly Gln Phe Glu Phe
    1610                1615                1620
Ile Cys Asp Glu Asn Asp Asn Ile Gln Pro Tyr Phe Ile Lys Phe
    1625                1630                1635
Asn Thr Leu Glu Thr Asn Tyr Thr Leu Tyr Val Gly Asn Arg Gln
    1640                1645                1650
Asn Met Ile Val Glu Pro Asn Tyr Asp Leu Asp Asp Ser Gly Asp
    1655                1660                1665
Ile Ser Ser Thr Val Ile Asn Phe Ser Gln Lys Tyr Leu Tyr Gly
    1670                1675                1680
```

-continued

```
Ile Asp Ser Cys Val Asn Lys Val Val Ile Ser Pro Asn Ile Tyr
1685                1690                1695
Thr Asp Glu Ile Asn Ile Thr Pro Val Tyr Glu Thr Asn Asn Thr
    1700                1705                1710
Tyr Pro Glu Val Ile Val Leu Asp Ala Asn Tyr Ile Asn Glu Lys
    1715                1720                1725
Ile Asn Val Asn Ile Asn Asp Leu Ser Ile Arg Tyr Val Trp Ser
    1730                1735                1740
Asn Asp Gly Asn Asp Phe Ile Leu Met Ser Thr Ser Glu Glu Asn
    1745                1750                1755
Lys Val Ser Gln Val Lys Ile Arg Phe Val Asn Val Phe Lys Asp
    1760                1765                1770
Lys Thr Leu Ala Asn Lys Leu Ser Phe Asn Phe Ser Asp Lys Gln
    1775                1780                1785
Asp Val Pro Val Ser Glu Ile Ile Leu Ser Phe Thr Pro Ser Tyr
    1790                1795                1800
Tyr Glu Asp Gly Leu Ile Gly Tyr Asp Leu Gly Leu Val Ser Leu
    1805                1810                1815
Tyr Asn Glu Lys Phe Tyr Ile Asn Asn Phe Gly Met Met Val Ser
    1820                1825                1830
Gly Leu Ile Tyr Ile Asn Asp Ser Leu Tyr Tyr Phe Lys Pro Pro
    1835                1840                1845
Val Asn Asn Leu Ile Thr Gly Phe Val Thr Val Gly Asp Asp Lys
    1850                1855                1860
Tyr Tyr Phe Asn Pro Ile Asn Gly Gly Ala Ala Ser Ile Gly Glu
    1865                1870                1875
Thr Ile Ile Asp Asp Lys Asn Tyr Tyr Phe Asn Gln Ser Gly Val
    1880                1885                1890
Leu Gln Thr Gly Val Phe Ser Thr Glu Asp Gly Phe Lys Tyr Phe
    1895                1900                1905
Ala Pro Ala Asn Thr Leu Asp Glu Asn Leu Glu Gly Glu Ala Ile
    1910                1915                1920
Asp Phe Thr Gly Lys Leu Ile Ile Asp Glu Asn Ile Tyr Tyr Phe
    1925                1930                1935
Asp Asp Asn Tyr Arg Gly Ala Val Glu Trp Lys Glu Leu Asp Gly
    1940                1945                1950
Glu Met His Tyr Phe Ser Pro Glu Thr Gly Lys Ala Phe Lys Gly
    1955                1960                1965
Leu Asn Gln Ile Gly Asp Tyr Lys Tyr Tyr Phe Asn Ser Asp Gly
    1970                1975                1980
Val Met Gln Lys Gly Phe Val Ser Ile Asn Asp Asn Lys His Tyr
    1985                1990                1995
Phe Asp Asp Ser Gly Val Met Lys Val Gly Tyr Thr Glu Ile Asp
    2000                2005                2010
Gly Lys His Phe Tyr Phe Ala Glu Asn Gly Glu Met Gln Ile Gly
    2015                2020                2025
Val Phe Asn Thr Glu Asp Gly Phe Lys Tyr Phe Ala His His Asn
    2030                2035                2040
Glu Asp Leu Gly Asn Glu Glu Gly Glu Glu Ile Ser Tyr Ser Gly
    2045                2050                2055
Ile Leu Asn Phe Asn Asn Lys Ile Tyr Tyr Phe Asp Asp Ser Phe
    2060                2065                2070
```

Thr Ala Val Val Gly Trp Lys Asp Leu Glu Asp Gly Ser Lys Tyr
            2075                2080                2085

Tyr Phe Asp Glu Asp Thr Ala Glu Ala Tyr Ile Gly Leu Ser Leu
            2090                2095                2100

Ile Asn Asp Gly Gln Tyr Tyr Phe Asn Asp Asp Gly Ile Met Gln
            2105                2110                2115

Val Gly Phe Val Thr Ile Asn Asp Lys Val Phe Tyr Phe Ser Asp
            2120                2125                2130

Ser Gly Ile Ile Glu Ser Gly Val Gln Asn Ile Asp Asp Asn Tyr
            2135                2140                2145

Phe Tyr Ile Asp Asp Asn Gly Ile Val Gln Ile Gly Val Phe Asp
            2150                2155                2160

Thr Ser Asp Gly Tyr Lys Tyr Phe Ala Pro Ala Asn Thr Val Asn
            2165                2170                2175

Asp Asn Ile Tyr Gly Gln Ala Val Glu Tyr Ser Gly Leu Val Arg
            2180                2185                2190

Val Gly Glu Asp Val Tyr Tyr Phe Gly Glu Thr Tyr Thr Ile Glu
            2195                2200                2205

Thr Gly Trp Ile Tyr Asp Met Glu Asn Glu Ser Asp Lys Tyr Tyr
            2210                2215                2220

Phe Asn Pro Glu Thr Lys Lys Ala Cys Lys Gly Ile Asn Leu Ile
            2225                2230                2235

Asp Asp Ile Lys Tyr Tyr Phe Asp Glu Lys Gly Ile Met Arg Thr
            2240                2245                2250

Gly Leu Ile Ser Phe Glu Asn Asn Asn Tyr Tyr Phe Asn Glu Asn
            2255                2260                2265

Gly Glu Met Gln Phe Gly Tyr Ile Asn Ile Glu Asp Lys Met Phe
            2270                2275                2280

Tyr Phe Gly Glu Asp Gly Val Met Gln Ile Gly Val Phe Asn Thr
            2285                2290                2295

Pro Asp Gly Phe Lys Tyr Phe Ala His Gln Asn Thr Leu Asp Glu
            2300                2305                2310

Asn Phe Glu Gly Glu Ser Ile Asn Tyr Thr Gly Trp Leu Asp Leu
            2315                2320                2325

Asp Glu Lys Arg Tyr Tyr Phe Thr Asp Glu Tyr Ile Ala Ala Thr
            2330                2335                2340

Gly Ser Val Ile Ile Asp Gly Glu Glu Tyr Tyr Phe Asp Pro Asp
            2345                2350                2355

Thr Ala Gln Leu Val Ile Ser Glu
            2360                2365

<210> SEQ ID NO 3
<211> LENGTH: 398
<212> TYPE: PRT
<213> ORGANISM: Clostridium perfringens
<220> FEATURE:
<221> NAME/KEY: mat_peptide
<222> LOCATION: (1)..(398)
<223> OTHER INFORMATION: Alpha toxin

<400> SEQUENCE: 3

Met Lys Arg Lys Ile Cys Lys Ala Leu Ile Cys Ala Ala Leu Ala Thr
1               5                   10                  15

Ser Leu Trp Ala Gly Ala Ser Thr Lys Val Tyr Ala Trp Asp Gly Lys
                20                  25                  30

Ile Asp Gly Thr Gly Thr His Ala Met Ile Val Thr Gln Gly Val Ser

-continued

```
               35                  40                  45
Ile Leu Glu Asn Asp Leu Ser Lys Asn Glu Pro Glu Ser Val Arg Lys
50                  55                  60

Asn Leu Glu Ile Leu Lys Glu Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asp Asn Asn Phe Ser Lys Asp Asn Ser Trp
                100                 105                 110

Tyr Leu Ala Tyr Ser Ile Pro Asp Thr Gly Glu Ser Gln Ile Arg Lys
                115                 120                 125

Phe Ser Ala Leu Ala Arg Tyr Glu Trp Gln Arg Gly Asn Tyr Lys Gln
130                 135                 140

Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Arg Lys Glu Gln Tyr Lys Ile
                180                 185                 190

Asn Thr Ala Gly Cys Lys Thr Asn Glu Ala Phe Tyr Thr Asp Ile Leu
                195                 200                 205

Lys Asn Lys Asp Phe Asn Ala Trp Ser Lys Glu Tyr Ala Arg Gly Phe
210                 215                 220

Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
                260                 265                 270

Glu Gly Asn Asp Pro Ser Val Gly Lys Asn Val Lys Glu Leu Val Ala
                275                 280                 285

Tyr Ile Ser Thr Ser Gly Glu Lys Asp Ala Gly Thr Asp Asp Tyr Met
                290                 295                 300

Tyr Phe Gly Ile Lys Thr Lys Asp Gly Lys Thr Gln Glu Trp Glu Met
305                 310                 315                 320

Asp Asn Pro Gly Asn Asp Phe Met Thr Gly Ser Lys Asp Thr Tyr Thr
                325                 330                 335

Phe Lys Leu Lys Asp Glu Asn Leu Lys Ile Asp Asp Ile Gln Asn Met
                340                 345                 350

Trp Ile Arg Lys Arg Lys Tyr Thr Ala Phe Ser Asp Ala Tyr Lys Pro
                355                 360                 365

Glu Asn Ile Lys Ile Ile Ala Asn Gly Lys Val Val Val Asp Lys Asp
                370                 375                 380

Ile Asn Glu Trp Ile Ser Gly Asn Ser Thr Tyr Asn Ile Lys
385                 390                 395
```